United States Patent [19]

Singh

[11] Patent Number: 4,859,232
[45] Date of Patent: Aug. 22, 1989

[54] SUBSTITUTED-ARYL CYCLOPROPANECARBONITRILES AND DERIVATIVES THEREOF AS HERBICIDE ANTIDOTES

[75] Inventor: Rajendra K. Singh, Chesterfield, Mo.

[73] Assignee: Monsanto Company, St. Louis, Mo.

[21] Appl. No.: 938,497

[22] Filed: Dec. 5, 1986

[51] Int. Cl.$^4$ ............................................. A01N 37/00
[52] U.S. Cl. .......................................... 71/100; 71/93; 71/105; 71/106; 558/426
[58] Field of Search ................... 558/426; 71/93, 100, 71/105, 106; 562/490, 460

[56] References Cited

U.S. PATENT DOCUMENTS 3,413,309 11/1968 Makosza et al. ................... 558/426
4,399,076 8/1983 Fayter et al. ......................... 558/426
4,562,213 12/1985 Nishida et al. ...................... 514/721
4,584,012 4/1986 Singh .................................... 71/100

OTHER PUBLICATIONS

Makosza et al., "ROCZ Chem.," vol. 49, pp. 297–305.
Abstract of Belg. 902147, 7/1985.
Roberts et al., "Jour. Organic Chemistry", vol. 35(4), (1970, pp. 978–981.

*Primary Examiner*—Anton H. Sutto
*Attorney, Agent, or Firm*—J. Timothy Keane; William I. Andress

[57] ABSTRACT

Substituted-aryl cyclopropanecarbonitriles and derivative compounds are antidotes for thiocarbamate, triazine-type and acetamide herbicides. These antidote compounds are especially effective in safening thiocarbamate herbicides used to control grassy weeds in wheat.

31 Claims, No Drawings

SUBSTITUTED-ARYL CYCLOPROPANECARBONITRILES AND DERIVATIVES THEREOF AS HERBICIDE ANTIDOTES

FIELD OF THE INVENTION

Herbicide antidotes are well-known crop protection chemicals. Of particular interest herein is a class of certain substituted-aryl cyclopropanecarbonitrile compounds and derivative compounds found effective as antidotes for protecting crop plants from herbicide injury.

BACKGROUND OF THE INVENTION

Many herbicides injure crop plants at herbicide application rates necessary to control weed growth. Accordingly, many herbicides cannot be used for controlling weeds in the presence of certain crops. Uncontrolled weed growth, however, results in lower crop yield and reduced crop quality inasmuch as weeds compete with crops for light, water and soil nutrients. Reduction of herbicidal injury to crops without an unacceptable corresponding reduction of herbicidal action on the weeds can be accomplished by use of crop protect ants known as herbicide "antidotes" or "safeners".

Certain substituted-aryl cyclopropanecarbonitrile compounds and derivatives are known. For example, the compound 1-naphthyl-1-cyclopropanecarbonitrile is shown in a publication of Makosza et al [*Rocz. Chem.*, 49, 297 (1975)], but without mention of any specific biological activity for this compound. U.S. Pat. No. 4,399,076 describes 1,1-disubstituted 2-vinyl/2-ethyl cyclopropanes as herbicides. Belgian Patent No. 900,594 describes certain halophenylcyclopropanecarbonitrile compounds, namely, 1-(2-fluorophenyl)cyclopropanecarbonitrile, 1-(4-fluorophenyl)cyclopropanecarbonitrile and 1-(4-chlorophenyl)cyclopropanecarbonitrile, as intermediates for preparation of triazoleethanol compounds used as fungicides. EPO Patent No. 94,085 describes the compound 4-chlorophenylcyclopropanecarboxylic acid as an intermediate for preparation of 1-(4-chlorophenyl)cyclopropanemethanol for use as an insecticide. Belgian Patent No. 902,147 describes 1-(4-ethoxyphenyl)cyclopropanecarbonitrile as an intermediate for preparation of compounds useful as pesticides. A publication of D. D. Roberts et al mentions the compound 1-(4-nitrophenyl)-cyclopropanecarboxylic acid for use in determination of cholsteryl tosylate solvolysis rates [*J. Org. Chem.*, 35 (4), 978–81 (1970)].

None of the foregoing patents or publications mentions any use of the described compounds as antidotes for herbicides.

An effective herbicide must provide a relatively high level of control of grassy or broad leaf weeds, or both, in the presence of crops in addition to meeting several other criteria. For example, the herbicide should possess relatively high unit activity so that lower rates of herbicide application are feasible. Lower application rates are desirable in order to minimize exposure of the environment to the herbicide. At the same time, such herbicide must be selective in herbicidal effect so as not to injure the crops. Herbicidal selectivity can be enhanced by use of an appropriate antidote in combination with the herbicide. But identification of an antidote which safens a herbicide in crops is a highly complicated task. Whether a compound or class of compounds provides efficacious antidote or safening activity is not a theoretical determination but must be done empirically. Safening activity is determined empirically by observing the complex interaction of several biological and chemical factors, namely: the type of herbicide compound; the type of weed to be controlled; the type of crop to be protected from weed competition and herbicidal injury; and the antidote compound itself. Moreover, the herbicide and antidote must each possess chemical and physical properties enabling preparation of a stable formulation which is environmentally safe and easy to apply to the field.

DESCRIPTION OF THE INVENTION

A family of compounds useful as antidotes against herbicide injury to crops is provided by substituted-aryl cyclopropanecarbonitrile compounds and derivative compounds embraced by general structural Formula I:

wherein A is selected from naphthyl, and

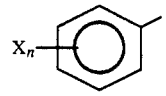

wherein each of $X_n$ is independently selected from halo, haloalkyl, alkoxycarbonyl, carboxylic acid, carboxylic acid salts of alkali metals, nitro, cyano, cyanocycloalkyl and phenoxy, with "n" being an integer from one through five, and wherein R is selected from cyano, carboxylic acid, carboxylic acid salts of alkali metals, carboxamide, N-alkylcarboxamide, N,N-dialkylcarboxamide and N-hydroxycarboximidamide.

A group of preferred antidote compounds within Formula I is provided by compounds wherein A is 2-naphthyl or $X_n$ wherein $X_n$ is one or more groups independently selected from halo, perhaloalkyl of one to three carbon atoms, cyano and cyanocycloalkyl, with "n" being one or two, and wherein R is cyano. Particularly preferred are those compounds wherein $X_n$ is one or more groups independently selected from chloro, bromo, iodo and trifluoromethyl, with "n" being one or two.

Another group of preferred antidote compounds within Formula I is provided by compounds wherein A is 1-naphthyl or $X_n$ wherein $X_n$ is one or more groups independently selected from fluoro, chloro, iodo and carboxylic acid, with "n" being one or two, and wherein R is selected from carboxylic acid, carboxamide and N-hydroxycarboximidamide.

The compounds of Formula I are believed to be structurally novel compounds with the proviso that when R is cyano, then A cannot be selected from 1-naphthyl, 2-fluorophenyl, 4-fluorophenyl, 4-chlorophenyl and 2,4-dichlorophenyl, and with the further proviso that when R is carboxylic acid, then A cannot be selected from 4-nitrophenyl, 4-chlorophenyl and 2,4-dichlorophenyl.

The phrase "substituted-aryl cyclopropylcarbonitrile compounds and derivative compounds" is a general phrase intended to embrace a class of antidote compounds defined by Formula I. All antidote compounds of this class are characterized in having a cyclopropyl group, one carbon of which is substituted with both a substituted-aryl group and a radical selected from cyano, carboxylic acid, carboxylic acid salt of alkali metals, carboxamide, N-alkylcarboxyamide, N,N-dialkylcarboxyamide and N-hydroxycarboximidamide. The term "substituted-aryl" denotes an aryl radical such as a phenyl group which is substituted at one or up to five of its substitutable positions with one or more radicals independently selected from halo, haloalkyl, alkoxycarbonyl, carboxylic acid, carboxylic acid salts of alkali metals, nitro, cyano, cyanocycloalkyl and phenoxy. The phenyl group may also be substituted or fused with another phenyl group to form a naphthyl group. The term "halo" embraces fluoro, chloro, bromo and iodo. Preferred halo groups are fluoro and chloro.

The term "haloalkyl" embraces radicals wherein any one or more of the carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are perhaloalkyl groups such as trifluoromethyl and perfluoroethyl groups. The term "alkoxycarbonyl" embraces linear or branched oxy-containing alkyl radicals attached to a carbonyl radical. The term "cyanocycloalkyl" embraces cyclized alkyl radicals of three to ten carbon atoms any one of which carbon atoms may be substituted by one or more cyano or cyanogen groups. The terms "nitro", "cyano" or "cyanogen", "carboxylic acid", "carboxamide", "carboximidamide" and "phenoxy" are self-defining. The term "carboxylic acid salts of alkali metals" includes carboxylate salts of metals such as lithium, sodium and potassium. Where the term "alkyl" is used within one of the aforementioned terms, "alkyl" is intended to embrace linear or branched radicals having one to ten carbon atoms, preferably one to five carbon atoms, unless otherwise specifically defined herein.

Also included in this invention are the stereo and optical isomers of compounds within the class defined by Formula I.

The terms "antidote", "safening agent", "safener", "antagonistic agent", "interferant", "crop protectant" and "crop protective", are often-used terms denoting a compound capable of reducing the phytotoxicity of a herbicide to a crop plant or crop seed. The terms "crop protectant" and "crop protective" are sometimes used to denote a herbicide-antidote combination which provides protection from competitive weed growth by reducing herbicidal injury to a valuable crop plant while at the same time controlling or suppressing weed growth occurring in the presence of the crop plant. Antidotes protect crop plants by interfering with the herbicidal action of a herbicide on the crop plants so as to render the herbicide selective to weed plants emerging or growing in the presence of crop plants.

Herbicides which may be used with benefit in combination with an antidote of the described class include thiocarbamates, triazines and acetamides. Such combinations can be used to obtain selective weed control with low crop injury in several varieties of monocotyledonous crop plants such as corn, grain sorghum (milo), and cereals such as wheat, rice, barley, oats and rye, as well as several varieties of dicotyledonous crop plants including oil-seed crops such as soybeans and cotton.

Examples of thiocarbamate herbicides are the following:

cis-/trans-2,3-dichloroallyl-diisopropylthiolcarbamate (common name "diallate");

ethyl dipropylthiocarbamate (common name "EPTC");

2,3,3-trichloroallyl-diisopropylthiolcarbamate (common name "triallate");

S-ethyl diisobutyl(thiocarbamate) (common name "butylate");

S-propyl dipropyl(thiocarbamate) (common name "vernolate").

Examples of triazine herbicides are the following:

2-chloro-4,6-bis(ethylamino)-1,3,5-triazine (common name "simazine");

2-chloro-4-ethylamino-6-isopropylamino-sym-triazine (common name "atrazine");

2-chloro-4-(1-cyano)-1-methyl(ethylamino)-6-ethylamino-1,3,5-triazine (common name "cyanazine").

Examples of acetamide herbicides are the following:

2-chloro-N-isopropylacetanilide (common name "propachlor");

2-chloro-2'-(1,1-dimethylethyl)-6'-methyl-N-(methoxymethyl)acetanilide;

N-(butoxymethyl)-2-chloro-N-[2-(1,1-dimethylethyl)-6-methylphenyl]acetamide (common name "terbuchlor");

2-chloro-2',6'-diethyl-N-(methoxymethyl)acetanilide (common name "alachlor");

2-chloro-N-(isobutoxymethyl)-2',6'-acetoxylidide;

2-chloro-2',6'-diethyl-N-(butoxymethyl)acetanilide (common name "butachlor");

2-chloro-N-(ethoxymethyl)-6'-ethyl-o-acetotoluidide (common name "acetochlor");

2-chloro-N-(2,6-dimethyl-1-cyclohexen-1-yl)-N-(2-ethoxyethyl)acetamide;

ethyl ester of N-chloroacetyl-N-(2,6-diethylphenyl) glycine (common name "diethatyl ethyl");

2-chloro-N-(2,6-dimethylphenyl)-N-(2-methoxyethyl) acetamide (common name "dimethachlor");

2-chloro-N-(2-methoxy-1-methylethyl)-6'-ethyl-o-acetotoluidide (common name "metolachlor");

2-chloro-2',3'-dimethyl-N-(isopropyl)acetanilide;

2-chloro-2'-methyl-6'-methoxy-N-(propoxymethyl)acetanilide;

2-chloro-2'-methyl-6'-methoxy-N-(isopropoxymethyl)acetanilide;

2-chloro-2'-methyl-6'-ethoxy-N-(propoxymethyl)acetanilide;

N-(ethoxymethyl)-N-(2-ethyl-6-methyl-1-cyclohexen-1-yl)-2-chloroacetamide;

N-(ethoxymethyl)-N-(2,5-dimethyl-1-cyclopenten-1-yl)-2-chloroacetamide;

2-chloro-2',6'-dimethyl-N-(1-pyrazol-1-ylmethyl)acetanilide (common name "metazachlor");

2-chloro-N-(2,6-dimethyl-1-cyclohexen-1-yl)-N-(1H-pyrazol-1-ylmethyl)acetamide;

2-chloro-6'-trifluoromethyl-N-(isopropoxymethyl)acetanilide;
2-chloro-2'-methyl-6'-trifluoromethyl-N-(ethoxymethyl)acetanilide;
2-chloro-2'-trifluoromethyl-6-methyl-N-(propoxymethyl)acetanilide;
2-chloro-2'-methyl-6'-trifluoromethyl-N-(isopropoxymethyl)acetanilide;
2-chloro-2'-(3-methylbutoxy)-6'-methyl-N-(methyl)acetanilide;
2-chloro-2'-isobutoxy-6'-methyl-N-(propoxymethyl)acetanilide;
2-chloro-2'-methyl-6'-propoxy-N-(methyl)acetanilide;
2-chloro-2'-butoxy-6'-methyl-N-(methyl)acetanilide;
α-chloro-N-(ethoxymethyl)-N-[2-methyl-1-(1-methylethyl)-1-propenyl]acetamide;
2-chloro-2'-ethyl-6'-(2-methylpropoxy)-N-(ethoxymethyl)acetanilide;
2-chloro-2'-methyl-6'-(1-methylbutoxy)-N-methylacetanilide;
2-chloro-2'-ethyl-6'-(1-methylpropyl)-N-methylacetanilide;
2-chloro-2'-(1,3-dimethylbutoxy)-6'-methyl-N-methylacetanilide;
2-chloro-2'-methyl-6'-(1-methylpropyl)-N-methylacetanilide;
2-chloro-2'-ethyl-6'-trifluoromethyl-N-(1-pyrazolyl-1-ylmethyl)acetanilide;
2-chloro-N-isopropyl-1-(3,5,5-trimethylcyclohexen-1-yl)acetamide (common name "trimexachlor").

Several of the mentioned herbicides are known in the art. Diallate and triallate herbicides are described in U.S. Pat. Nos. 3,330,643 and 3,330,821. Atrazine herbicide is described in U.K. Pat. No. 814,947. Alachlor, butachlor and acetochlor herbicides are described in U.S. Pat. Nos. 3,442,945 or 3,547,620. Propachlor herbicide is described in U.S. Pat. No. 2,863,752 and Reissue Pat. No. 26,961. Metolachlor herbicide is described in U.S. Pat. No. 3,937,730. Metazachlor herbicide is described in U.S. Pat. No. 4,249,935. Trimexachlor herbicide is described in U.S. Pat. No. 4,319,918. U.S. Pat. No. 4,351,667 describes the herbicides N-(ethoxymethyl)-N-(2-ethyl-6-methyl-1-cyclohexen-1-yl)-2-chloroacetamide and N-(ethoxymethyl)-N-2-(2,5-dimethyl-1-cyclopenten-1-yl)-2-chloroacetamide. U.K. Pat. No. 2,072,175 describes the herbicide 2-chloro-2'-methyl-6'-methoxy-N-(isopropoxymethyl)acetanilide. U.K. Pat. No. 2,072,181 describes the herbicide 2-chloro-2'-methyl-6'-trifluoromethyl-N-(ethoxymethyl)acetanilide.

Combinations may be made of any one or more of the described antidote compounds with any one or more of the herbicide compounds mentioned herein.

Antidote compounds of the class defined by Formula I reduce herbicidal injury to grain sorghum (milo), wheat, rice, soybean and corn, especially where herbicide injury is associated with pre-emergent application of the herbicides. Antidote compounds of the invention have been found particularly effective to reduce injury to wheat caused by thiocarbamate herbicides such as triallate.

ANTIDOTE COMPOUND PREPARATION

The antidote compounds of the invention may be prepared by one of the following General Procedures A-D:

The specific examples following General Procedures A-D are presented for purposes of illustration only and are not intended as a restriction on the scope of the invention. All parts are by weight unless otherwise indicated. Most of the commercially-available starting materials were obtained from Aldrich Chemical Co., Milwaukee, Wis. Table I sets forth analytical data for 43 specific compounds prepared in accordance with these procedures.

Procedure A:

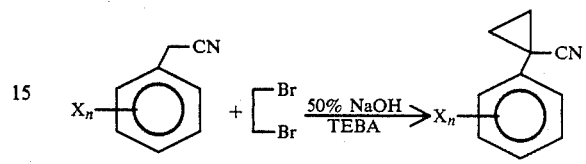

where $X_n$=2-fluoro; 3-fluoro; 4-fluoro; 2-fluoro; 4-fluoro; 2-chloro; 3-chloro; 2-bromo; 3-bromo; 4-bromo; 2-iodo; 3-iodo; 4-iodo; 4-chloro; 6-fluoro; 2,4-dichloro; 2,6-difluoro; 2,4-dichloro; 3,4-dichloro; 2,6-dichloro; 2,3,6-trichloro; 2-CF$_3$; 3-CF$_3$; 4-CF$_3$; 2-CH$_3$; 3-CH$_3$; 2,3-benzo; 3,4-benzo; 2-(1-cyanocyclopropyl); 2-CN; 4-CN; 3-carbethoxy; 3-NO$_2$; 3,5-dimethoxy; 3-phenoxy.

TEBA=triethylbenzylammonium chloride

EXAMPLE I

Preparation of 1-[3-(trifluoromethyl)phenyl]cyclopropane carbonitrile (Antidote Compound #20)

To a mixture of 3-(trifluoromethyl)phenylacetonitrile (18.5 g, 0.1 mole), 1,2-dibromoethane (56.4 g, 0.3 mole) and triethylbenzylammonium chloride (TEBA) (1.0 g), there was added 40 ml of 50% sodium hydroxide solution at room temperature. The exothermic reaction mixture was vigorously stirred overnight. The reaction mixture was diluted with water (100 ml) and extracted with ether (4×100 ml). The organic layer was washed with water (3×50 ml), brine (50 ml) and dried over magnesium sulfate. The solvent was removed and the product was distilled under reduced pressure (B.P. 92°-94° C. at 0.4 mm Hg) to give a 16.7 g of product (79% yield).

Procedure B:

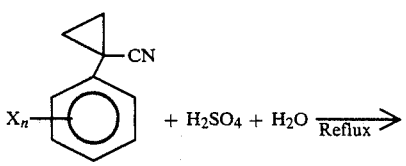

where $X_n$ is 4-chloro; 2-bromo; 3-bromo; 2-iodo; 3-iodo; 4-iodo; 3-carboxylic acid; 3-NO$_3$; 2,3-benzo.

EXAMPLE II

Preparation of 1-(4-iodophenyl)cyclopropanecarboxylic acid (Antidote Compound #38)

To a mixture of concentrated sulfuric acid (20 ml) and water (30 ml) at room temperature, there was added 1-(4-iodophenyl)cyclopropanecarbonitrile (7.0 g, 0.026 m). The reaction mixture was refluxed for 15 hrs under nitrogen atmosphere. The reaction mixture was cooled to room temperature and extracted with ether-chloroform mixture (4×100 ml). The organic layer was washed with water (2×50 ml), brine (50 ml) and dried over magnesium sulfate. The solvent was removed to give 7.2 g of product (96% yield; M.P. 150°–152° C.).

Procedure C:

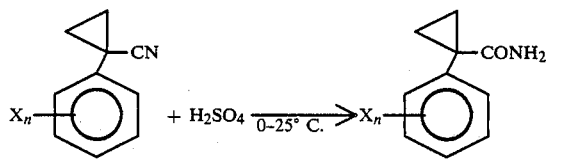

$X_n$ = 2-chloro, 6-fluoro.

EXAMPLE III

Preparation of 1-(2-chloro-6-fluorophenyl)cyclopropanecarboxamide (Antidote Compound #42)

A reaction vessel containing 25 ml of concentrated sulfuric acid was cooled in ice bath. Then, 1-(2-chloro-6-fluorophenyl)cyclopropane carbonitrile (8.9 g, 0.046 mole) was slowly added to the reaction vessel. The reaction mixture was allowed to 15 warm to room temperature and stirred for 2½ days. The mixture was poured into 100 ml of ice water mixture and then extracted with methylene chloride. The organic layer was washed with water (2×100 ml), brine (100 ml) and dried over magnesium sulfate. The solvent was removed and the product was chromatographed over 120 g silica gel with a cyclohexane:ethyl acetate (70:30) eluent to give 7.6 g of product (M.P. 98°–102° C.).

Procedure D:

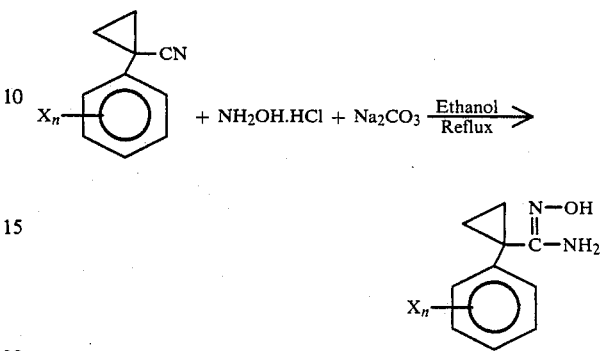

where $X_n$ = 2-bromo

EXAMPLE IV

Preparation of 1-(2-bromophenyl)-N-hydroxycyclopropanecarboximidamide (Antidote Compound #43)

To a solution of 1-(2-bromophenyl)cyclopropanecarbonitrile (19.6 g, 0.1 mole) in ethanol (100 ml), there was added water (100 ml) and then added hydroxylamine hydrochloride (14.0 g, 0.2 mole) and finally added sodium carbonate (11.0 g, 0.1 mole). The reaction mixture was refluxed for 16 hrs. The reaction mixture was cooled to room temperature and water (100 ml) was added. A white precipitate formed and was filtered to give 9.39 g of product (36% yield; M.P. 164°–167° C.).

The following antidote compounds of Table I were synthesized in accordance with one of the foregoing general procedures, and the respective specific exemplification, as indicated in the column headed "Method of Preparation".

TABLE I

| Antidote Example Compound # | Name | Yield (%) | Structure | Method of Prep. | Analysis (%) Calc'd | Found | M.P./B.P. °C. |
|---|---|---|---|---|---|---|---|
| 1 | 1-(2-fluorophenyl)cyclopropane-carbonitrile | 72 | (2-F-C6H4)-cyclopropane-CN | A | C 74.52<br>H 5.00<br>N 8.69 | 74.59<br>5.04<br>8.64 | 126–128<br>@5.00mm |
| 2 | 1-(3-fluorophenyl)cyclopropane-carbonitrile | 71 | (3-F-C6H4)-cyclopropane-CN | A | C 74.52<br>H 5.00<br>N 8.69 | 74.46<br>5.05<br>8.67 | 63–64 |
| 3 | 1-(4-fluorophenyl)cyclopropane-carbonitrile | 48 | (4-F-C6H4)-cyclopropane-CN | A | C 74.52<br>H 5.00<br>N 8.69 | 74.67<br>5.07<br>8.61 | 155<br>@4.5mm |
| 4 | 1-(2-chlorophenyl)cyclopropane-carbonitrile | 80 | (2-Cl-C6H4)-cyclopropane-CN | A | C 67.62<br>H 4.54<br>N 7.89 | 67.49<br>4.58<br>7.84 | 105–106<br>@0.80mm |
| 5 | 1-(3-chlorophenyl)cyclopropane-carbonitrile | 76 | (3-Cl-C6H4)-cyclopropane-CN | A | C 67.62<br>H 4.54<br>Cl 19.96 | 67.51<br>4.58<br>19.82 | 105–107<br>@0.80t |
| 6 | 1-(4-chlorophenyl)cyclopropane-carbonitrile | — | (4-Cl-C6H4)-cyclopropane-CN |  | [KNOWN COMPOUND] |  | 50 |
| 7 | 1-(2-bromophenyl)cyclopropane-carbonitrile | 77 | (2-Br-C6H4)-cyclopropane-CN | A | C 54.08<br>H 3.63<br>N 6.31 | 54.07<br>3.66<br>6.30 | 131–135<br>@0.80mm |

TABLE I-continued

| Antidote Example Compound # | Name | Yield (%) | Structure | Method of Prep. | Analysis (%) Calc'd | Analysis (%) Found | M.P./B.P. °C. |
|---|---|---|---|---|---|---|---|
| 8 | 1-(3-bromophenyl)cyclopropane-carbonitrile | 67 | 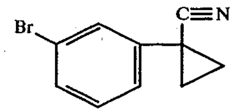 | A | C 54.08<br>H 3.63<br>Br 35.98<br>N 6.31 | 53.87<br>3.65<br>35.94<br>6.29 | 44-46<br>95-103<br>@0.20mm |
| 9 | 1-(4-bromophenyl)cyclopropane-carbonitrile | 47 | 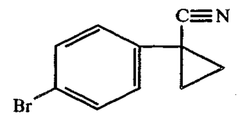 | A | C 54.08<br>H 3.63<br>N 6.31 | 54.05<br>3.65<br>6.26 | 61-63 |
| 10 | 1-(2-iodophenyl)cyclopropane-carbonitrile | 74 | 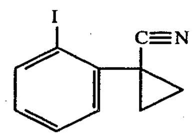 | A | C 44.64<br>H 3.00<br>N 5.21 | 44.55<br>3.03<br>5.19 | 82-83 |
| 11 | 1-(3-iodophenyl)cyclopropane-carbonitrile | 84 | 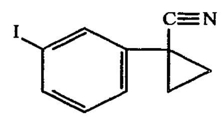 | A | C 44.64<br>H 3.00<br>N 5.21 | 44.44<br>3.07<br>5.14 | 130-133<br>@0.80mm |
| 12 | 1-(4-iodophenyl)cyclopropane-carbonitrile | 59 | 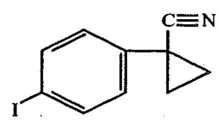 | A | C 44.64<br>H 3.00<br>N 5.21 | 44.64<br>3.05<br>5.16 | 96-97 |
| 13 | 1-(2,6-difluorophenyl)cyclo-propanecarbonitrile | 65 | 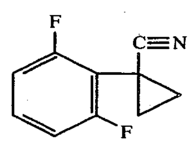 | A | C 67.04<br>H 3.94<br>N 7.82 | 66.78<br>3.97<br>7.73 | 53-57 |
| 14 | 1-(2-chloro-6-fluorophenyl)-cyclopropanecarbonitrile | 54 | 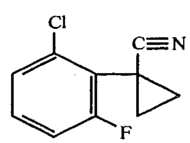 | A | C 61.40<br>H 3.61<br>Cl 18.12<br>N 7.16 | 61.34<br>3.64<br>18.08<br>7.14 | 59-60 |

TABLE I-continued

| Antidote Example Compound # | Name | Yield (%) | Structure | Method of Prep. | Analysis (%) Calc'd | Analysis (%) Found | M.P./B.P. °C. |
|---|---|---|---|---|---|---|---|
| 15 | 1-(2,4-dichlorophenyl)cyclopropanecarbonitrile | 72 | 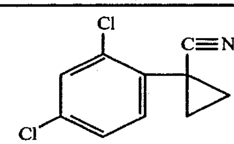 | A | C 56.63<br>H 3.33<br>N 6.60 | 56.65<br>3.33<br>6.57 | 81-82 |
| 16 | 1-(3,4-dichlorophenyl)cyclopropanecarbonitrile | 75 | 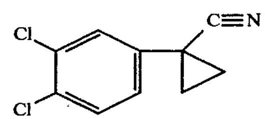 | A | C 56.63<br>H 3.33<br>N 6.60 | 56.69<br>3.35<br>6.53 | 85-86 |
| 17 | 1-(2,6-dichlorophenyl)cyclopropanecarbonitrile | 55 | 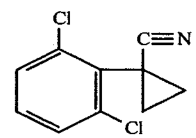 | A | C 56.63<br>H 3.33<br>Cl 33.43<br>N 6.60 | 56.50<br>3.33<br>33.34<br>6.54 | 62-65 |
| 18 | 1-(2,3,6-trichlorophenyl)cyclopropanecarbonitrile | 74 | 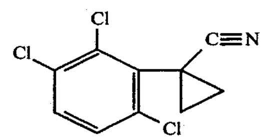 | A | C 48.72<br>H 2.45<br>Cl 43.14 | 48.70<br>2.47<br>43.09 | 114-115 |
| 19 | 1-[2-(trifluoromethyl)phenyl]-cyclopropanecarbonitrile | 94 | 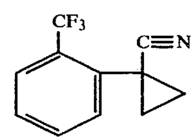 | A | C 62.56<br>H 3.82<br>N 6.63 | 62.48<br>3.85<br>6.62 | 92-94 0.9mm |
| 20 | 1-[3-(trifluoromethyl)phenyl]-cyclopropanecarbonitrile | 79 | 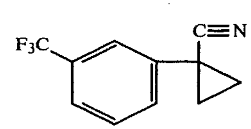 | A | C 62.56<br>H 3.82<br>N 6.63 | 62.49<br>3.86<br>6.61 | 92-94 @0.40mm |
| 21 | 1-[4-(trifluoromethyl)phenyl]-cyclopropanecarbonitrile | 91 | 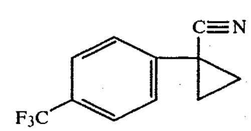 | A | C 62.56<br>H 3.82<br>N 6.63 | 62.48<br>3.87<br>6.63 | 96@ 0.80mm |

TABLE I-continued

| Antidote Example Compound # | Name | Yield (%) | Structure | Method of Prep. | Analysis (%) Calc'd | Analysis (%) Found | M.P./B.P. °C. |
|---|---|---|---|---|---|---|---|
| 22 | 1-(2-methylphenyl)cyclopropane-carbonitrile | 39 | 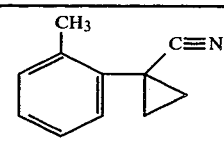 | A | C 84.04<br>H 7.05 | 83.93<br>7.05 | 105–107<br>@2.00mm |
| 23 | 1-(3-methylphenyl)cyclopropane-carbonitrile | 43 | 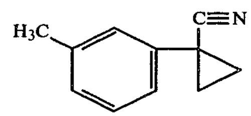 | A | C 84.04<br>H 7.05<br>N 8.91 | 84.01<br>7.06<br>8.89 | 91–97<br>@0.20mm |
| 24 | 1-(1-naphthalenyl)cyclopropane-carbonitrile | 39 | 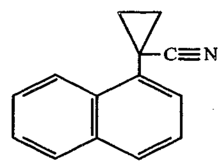 | A | C 87.01<br>H 5.74<br>N 7.25 | 87.00<br>5.63<br>7.23 | 81–82 |
| 25 | 1-(2-naphthalenyl)cyclopropane-carbonitrile | 61 | 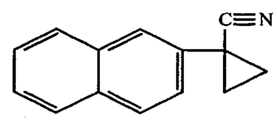 | A | C 87.01<br>H 5.74<br>N 7.25 | 86.91<br>5.79<br>7.19 | 165<br>@1.50mm |
| 26 | 1-(3-carbethoxyphenyl)cyclopropanecarbonitrile | 81 | 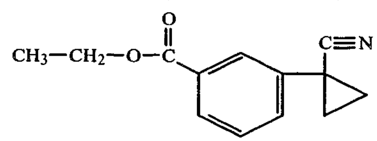 | A | C 72.54<br>H 6.09<br>N 6.51 | 72.51<br>6.10<br>6.47 | 159<br>1.80mm |
| 27 | 1-(2-cyanophenyl)cyclopropane-carbonitrile | 30 | .1/10 H₂O | A | C 77.72<br>H 4.86 | 77.35<br>4.93 | 95–100 |
| 28 | 1-(4-cyanophenyl)cyclopropane-carbonitrile | 71 | 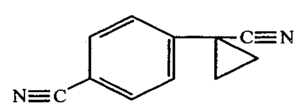 | A | C 78.55<br>H 4.79<br>N 16.66 | 78.35<br>4.81<br>16.61 | 110–114 |

TABLE I-continued

| Antidote Example Compound # | Name | Yield (%) | Structure | Method of Prep. | Analysis (%) Calc'd | Analysis (%) Found | M.P./B.P. °C. |
|---|---|---|---|---|---|---|---|
| 29 | 1-[2-(1-cyanocylopropyl)phenyl]-cyclopropanecarbonitrile | 30 | 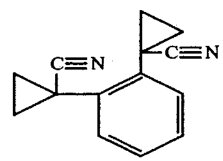 | A | C 80.74<br>H 5.81<br>N 13.45 | 80.61<br>5.88<br>13.41 | |
| 30 | 1-(3-nitrophenyl)cyclopropane-carbonitrile | 67 | 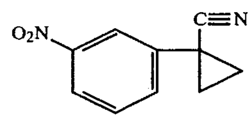 | A | C 63.83<br>H 4.29<br>N 14.89 | 63.76<br>4.30<br>14.80 | 94-96 |
| 31 | 1-(3-phenoxyphenyl)cyclopropane-carbonitrile | 70 | 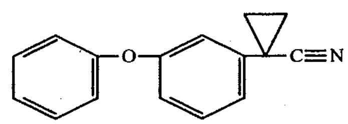 | A | C 81.68<br>H 5.57<br>N 5.95 | 81.54<br>5.62<br>5.90 | 170@<br>1.20mm |
| 32 | 1-(3,5-dimethoxyphenyl)cyclo-propanecarbonitrile | 70 | 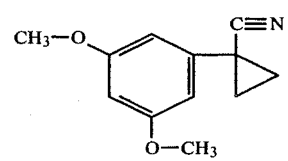 | A | C 70.92<br>H 6.45<br>N 6.89 | 71.00<br>6.47<br>6.84 | 51-54 |
| 33 | 1-(4-chlorophenyl)cyclopropane-carboxylic acid | — | 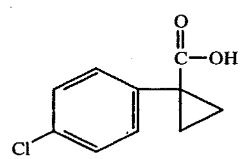 | | [KNOWN COMPOUND] | | 150 |
| 34 | 1-(2-bromophenyl)cyclopropane-carboxylic acid | 78 | 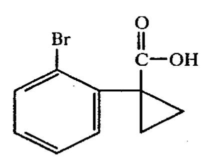 | B | C 49.82<br>H 3.76<br>Br 33.15 | 49.78<br>3.80<br>33.09 | 159-163 |

TABLE I-continued

| Antidote Example Compound # | Name | Yield (%) | Structure | Method of Prep. | Analysis (%) Calc'd | Analysis (%) Found | M.P./B.P. °C. |
|---|---|---|---|---|---|---|---|
| 35 | 1-(3-bromophenyl)cyclopropane-carboxylic acid | 62 | 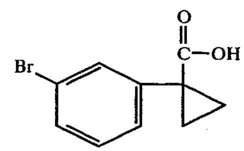 | B | C 49.82<br>H 3.76<br>Br 33.15 | 49.81<br>3.79<br>33.23 | 139–143 |
| 36 | 1-(2-iodophenyl)cyclopropane-carboxylic acid | 73 | 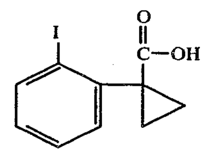 | B | C 41.69<br>H 3.15<br>I 44.05 | 41.79<br>3.17<br>44.13 | 163–168 |
| 37 | 1-(3-iodophenyl)cyclopropane-carboxylic acid | 91 | 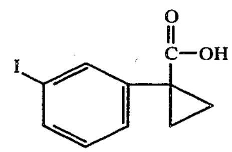 | B | C 41.69<br>H 3.15<br>I 44.05 | 41.79<br>3.18<br>44.14 | 121–12 |
| 38 | 1-(4-iodophenyl)cyclopropane-carboxylic acid | 96 | 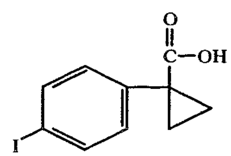 | B | C 41.69<br>H 3.15<br>I 44.05 | 41.73<br>3.17<br>44.12 | 150–152 |
| 39 | 1-(1-naphthalenyl)cyclopropane-carboxylic acid | 55 | 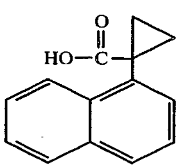 | B | C 79.23<br>H 5.70 | 79.69<br>6.06 | 155–160 |
| 40 | 3-(1-carboxycyclopropyl)benzoic acid | 100 | 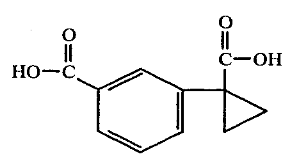 | B | C 64.08<br>H 4.89 | 64.09<br>4.93 | 247–248 |

TABLE 1-continued

| Antidote Example Compound # | Name | Yield (%) | Structure | Method of Prep. | Analysis (%) Calc'd | Found | M.P./B.P. °C. |
|---|---|---|---|---|---|---|---|
| 41 | 1-(3-nitrophenyl)cyclopropane-carboxylic acid | 50 | (3-nitrophenyl cyclopropane with COOH) | B | C 57.97<br>H 4.38<br>N 6.76 | 58.01<br>4.40<br>6.74 | 177–81 |
| 42 | 1-(2-chloro-6-fluorophenyl)cyclopropanecarboxamide | 77 | (2-chloro-6-fluorophenyl cyclopropane with CONH$_2$) | C | C 56.22<br>H 4.25<br>Cl 16.59<br>N 6.56 | 56.59<br>4.13<br>16.87<br>6.17 | 98–102 |
| 43 | 1-(2-bromophenyl)-N—hydroxycyclopropanecarboximidamide | 36 | (2-bromophenyl cyclopropane with C(NH$_2$)=N—OH) | D | C 47.08<br>H 4.35<br>Br 31.32<br>N 10.98 | 46.92<br>4.35<br>31.24<br>10.92 | 164–167 |

BIOLOGICAL EVALUATION

Effective weed control coupled with low crop injury is a result of treatment of a plant locus with a combination of herbicide compound and antidote compound. By application to the "plant locus" is meant application to the plant growing medium, such as soil, as well as to the seeds, emerging seedlings, roots, stems, leaves, or other plant parts.

The phrase "combination of herbicide compound and antidote compound" embraces various methods of treatment. For example, the soil of a plant locus may be treated with a "tank-mix" composition containing a mixture of the herbicide and the antidote which is "in combination". Or, the soil may be treated with the herbicide and antidote compounds separately so that the "combination" is made on, or in, the soil. After such treatments of the soil with a mixture of herbicide and antidote or by separate or sequential application of the herbicide and antidote to the soil, the herbicide and antidote may be mixed into or incorporated into the soil either by mechanical mixing of the soil with implements or by "watering in" by rainfall or irrigation. The soil of a plant locus may also be treated with antidote by application of the antidote in a dispersible-concentrate form such as a granule. The granule may be applied to a furrow which is prepared for receipt of the crop seed and the herbicide may be applied to the plant locus either before or after in-furrow placement of the antidote-containing granule so that the herbicide and antidote form a "combination". Crop seed may be treated or coated with the antidote compound either while the crop seed is in-furrow just after seeding or, more commonly, the crop seed may be treated or coated with antidote prior to seeding into a furrow. The herbicide may be applied to the soil plant locus before or after seeding and a "combination" is made when both herbicide and antidote-coated seed are in the soil. Also contemplated as a "combination" is a commercially-convenient association or presentation of herbicide and antidote. For example, the herbicide and antidote components in concentrated form may be contained in separate containers, but such containers may be presented for sale or sold together as a "combination". Or, the herbicide and antidote components in concentrated form may be in a mixture in a single container as a "combination". Either such "combination" may be diluted or mixed with adjuvants suitable for soil applications. Another example of a commercially-presented combination is a container of antidote-coated crop seed sold, or presented for sale, along with a container of herbicide material. These containers may, or may not, be physically attached to each other, but nonetheless constitute a "combination of herbicide and antidote" when intended for use ultimately in the same plant locus.

The amount of antidote employed in the methods and compositions of the invention will vary depending upon the particular herbicide with which the antidote is employed, the rate of application of the herbicide, the particular crop to be protected, and the manner of application to the plant locus. In each instance the amount of antidote employed is a safening-effective amount, that is, the amount which reduces, or protects against, crop injury that otherwise would result from the presence of the herbicide. The amount of antidote employed will be less than an amount that will substantially injure the crop plant.

The antidote can be applied to the crop plant locus in a mixture with the selected herbicide. For example, where the crop seed is first planted, a suitable mixture of antidote and herbicide, whether in a homogeneous liquid, emulsion, suspension or solid form, can be applied to the surface of, or incorporated in, the soil in which the seed has been planted. Or, the herbicide-antidote mixture may be applied to the soil, and then the seed thereafter "drilled" into the soil below the soil layer containing the herbicide-antidote mixture. The herbicide will reduce or eliminate the presence of undesirable weed plants. Where the herbicide would by itself injure the crop seedlings, the presence of the antidote will reduce or eliminate the injury to the crop seed caused by the herbicide. It is not essential that the application of herbicide and the antidote to the plant locus be made using the selected herbicide and antidote in the form of a mixture or composition. The herbicide and the antidote may be applied to the plant locus in a sequential manner. For example, the antidote may be first applied to the plant locus and thereafter the herbicide is applied. Or, the herbicide may be first applied to the plant locus and thereafter the antidote is applied.

The ratio of herbicide to antidote may vary depending upon the crop to be protected, weed to be inhibited, herbicide used, etc., but normally a herbicide-to-antidote ratio ranging from 1:25-to-50:1 (preferably 1:5-to 30:1) parts by weight may be employed. As indicated above, the antidote may be applied to the plant locus in a mixture, i.e., a mixture of a herbicidally-effective amount of herbicide and a safening-effective amount of an antidote, or sequentially, i.e., the plant locus may be treated with an effective amount of the herbicide followed by a treatment with the antidote or vice versa. In general, effective herbicidal amounts are in the range of about 0.1 to about 12 kilograms/hectare. The preferred range of rate of application is from about 0.4 to about 10 Kg/h. Preferably, antidote application rates range from about 0.5 Kg/ha down to about 0.05 Kg/ha. It will be appreciated that at times amounts either below or above these ranges will be necessary to obtain the best results. The selection of the herbicide to inhibit the emergence and growth of weeds depends upon the species of weeds to be controlled and the crop to be protected.

The application of the antidote can be made directly to the seed before planting. In this practice, a quantity of crop seed is first coated with the antidote. The coated seed is thereafter planted. The herbicide may be applied to the soil before or after the coated seed is planted.

Evaluations of safening activity of the antidote compounds of this invention were carried out using the specific procedures of Examples V–VII in greenhouse testing. Measurements of biological response as reported in Tables II–IV were made in the following manner. A visual comparison was made between a crop plant treated with herbicide alone and crop plant having no herbicide or antidote treatment. A number was assigned to this visual comparison indicating the percent injury or inhibition to the herbicide-alone treated crop plant (column "WO" in Tables II–IV indicating herbicide "without" antidote). Also, a visual comparison was made between the crop plant treated with herbicide+antidote combination and the crop plant having no herbicide or antidote treatment. A number was assigned to this visual comparison indicating the percent injury or inhibition to the herbicide+antidote treated crop plant (column "W" in Tables II–IV indicating herbicide "with" antidote). Where treatments involved weed plant species, observations of response to herbicide or herbicide+antidote were similarly recorded. The degree of reduction of herbicide injury provided by an antidote compound is indicated by the magnitude that the plant inhibition number of column "WO" exceeds the corresponding number of column "W". Also reported in Tables II-IV are data showing "safening effect" for the herbicide+antidote combinations calculated from the plant inhibition numbers. These tables show crop or weed column headings under which there are no data. The lack of such data is not an indication of a failed test; rather it is merely an indication that the particular herbicide+antidote rate combination was not tested with that crop or weed. Summarized below is key information for interpreting data reported in Tables II-IV:

| Herbicide No. | Name |
|---|---|
| 1 | 2,3,3-trichloroallyldiisopropylthiocarbamate (triallate) |
| 2 | 2-chloro-4-ethylamino-6-isopropylamino-1,3,5-triazine (atrazine) |
| 3 | 2-chloro-2',6'-diethyl-N—(methoxymethyl)-acetanilide (alachlor) |
| 4 | 2-chloro-2',6'-diethyl-N—(butoxymethyl)-acetanilide (butachlor) |
| 5 | 2-chloro-2'-methyl-6'-methoxy-N—(isopropoxymethyl)acetanilide |

Antidote No. = Compound in corresponding Example No.
Rate = Kilograms/hectare (Kg/ha).
W = % Plant Inhibition caused by combination of herbicide and antidote.
WO = % Plant Inhibition caused by herbicide alone.
Data reported in parentheses = % Safening Effect
$(\_) = \frac{WO - W}{WO} \times 100$

EXAMPLE V

The following procedure shows interaction between herbicide and antidote when both are incorporated in a soil cover layer before emergence of crop and weed species. Containers were filled and compacted with a fumigated silt loam top soil to a depth of about 1.3 cm from the top of the container. A first container was designated as an untreated control, a second container was designated as a herbicide control, and a third container was designated as a herbicide+antidote test container. Each of the containers was seeded with a crop species. A measured amount of herbicide dispersed or dissolved in acetone was applied to a measured quantity of soil. To this same quantity of soil treated with herbicide, there was added a measured amount of antidote dispersed or dissolved in acetone. The quantity of soil treated with the herbicide and antidote was thoroughly mixed to incorporate the herbicide and antidote in the soil uniformly. The seed bed in the third container of soil was covered with the soil treated with the herbicide and antidote and the container was leveled. For each test series, the seed beds of the first and second containers were likewise covered by soil layers. The cover layer of the first container was not treated with herbicide or antidote. The cover layer of the second container had a measured quantity of herbicide alone incorporated therein. The containers were then placed on a bench in a greenhouse and sub-irrigated as required for the duration of the test. Plant response was observed about three weeks after initial treatment. Results are reported in Table II.

TABLE II

| % PLANT INHIBITION AND % SAFENING EFFECT ( ) | | | | | | | | |
|---|---|---|---|---|---|---|---|---|
| HERBICIDE | | ANTIDOTE | | RICE | SORGHUM | GRAIN WHEAT | SOYBEAN | CORN |
| NO. | RATE | NO. | RATE | W WO | W WO | W WO | W WO | W WO |
| 1 | 0.56 | 6 | 8.96 | 90 90 (0) | 90 88 (0) | 100 100 (0) | | |
| 1 | 0.56 | 33 | 8.96 | 90 90 (0) | 85 88 (3) | 90 100 (10) | | |
| 1 | 100 | 20 | 8.96 | | 40 98 (59) | | | |
| 1 | 0.56 | 24 | 8.96 | | | 75 98 (23) | | |
| 1 | 0.56 | 3 | 8.96 | | | 85 95 (10) | | |
| 1 | 0.56 | 39 | 8.96 | | | 100 100 (0) | | |
| 1 | 0.56 | 29 | 8.96 | | | 70 99 (29) | | |
| 1 | 0.56 | 25 | 8.96 | | | 90 100 (10) | | |
| 1 | 0.56 | 17 | 8.96 | | | 35 100 (65) | | |
| 1 | 0.56 | 15 | 8.96 | | | 50 100 (50) | | |
| 1 | 0.56 | 14 | 8.96 | | | 25 90 (72) | | |
| 1 | 0.56 | 27 | 8.96 | | | 95 90 (0) | | |
| 1 | 0.56 | 4 | 8.96 | | | 10 90 (88) | | |
| 1 | 0.56 | 1 | 8.96 | | | 80 90 (11) | | |
| 1 | 0.56 | 22 | 8.96 | | | 90 95 (5) | | |
| 1 | 0.56 | 5 | 8.96 | | | 100 (0) | 95 | |
| 1 | 0.56 | 18 | 8.96 | | | 85 90 (5) | | |

TABLE II-continued

% PLANT INHIBITION AND % SAFENING EFFECT ( )

| HERBICIDE | | ANTIDOTE | | RICE | SORGHUM | GRAIN WHEAT | SOYBEAN | CORN |
|---|---|---|---|---|---|---|---|---|
| NO. | RATE | NO. | RATE | W WO | W WO | W WO | W WO | W WO |
| 1 | 0.56 | 2 | 8.96 | | | 70 85 (17) | | |
| 1 | 0.56 | 16 | 8.96 | | | 80 95 (15) | | |
| 1 | 0.56 | 42 | 8.96 | | | 100 95 (0) | | |
| 1 | 0.56 | 21 | 8.96 | | | 45 90 (50) | | |
| 1 | 0.56 | 19 | 8.96 | | | 80 90 (11) | | |
| 1 | 0.56 | 13 | 8.96 | | | 75 85 (11) | | |
| 1 | 0.56 | 9 | 8.96 | | | 80 100 (20) | | |
| 1 | 0.56 | 30 | 8.96 | | | 90 100 (10) | | |
| 1 | 0.56 | 23 | 8.96 | | | 65 80 (18) | | |
| 1 | 0.56 | 10 | 8.96 | | | 45 90 (50) | | |
| 1 | 0.56 | 7 | 8.96 | | | 80 100 (20) | | |
| 1 | 0.56 | 11 | 8.96 | | | 70 100 (30) | | |
| 1 | 0.56 | 12 | 8.96 | | | 40 95 (57) | | |
| 1 | 0.56 | 26 | 8.96 | | | 100 95 (0) | | |
| 1 | 0.56 | 8 | 8.96 | | | 40 90 (55) | | |
| 1 | 0.56 | 37 | 8.96 | | | 100 90 (0) | | |
| 1 | 0.56 | 34 | 8.96 | | | 100 100 (0) | | |
| 1 | 0.56 | 38 | 8.96 | | | 100 90 (0) | | |
| 1 | 0.56 | 40 | 8.96 | | | 100 90 (0) | | |
| 1 | 0.56 | 36 | 8.96 | | | 100 95 (0) | | |
| 1 | 0.56 | 35 | 8.96 | | | 100 100 (0) | | |
| 1 | 0.56 | 32 | 8.96 | | | 90 75 (0) | | |
| 2 | 6.72 | 20 | 8.96 | 70 75 (6) | | | 90 90 (0) | |
| 2 | 6.72 | 24 | 8.96 | 40 40 (0) | | | 98 97 (0) | |
| 2 | 6.72 | 3 | 8.96 | 70 85 (17) | | | 85 95 (10) | |
| 2 | 6.72 | 39 | 8.96 | 90 80 (0) | | | 90 98 (8) | |
| 2 | 6.72 | 29 | 8.96 | 60 70 (14) | | | 95 90 (0) | |
| 2 | 6.72 | 25 | 8.96 | 90 95 (5) | | | 100 98 (0) | |
| 2 | 4.48 | 17 | 8.96 | 90 90 (0) | | | 90 95 (5) | |
| 2 | 4.48 | 15 | 8.96 | 90 90 (0) | | | 90 95 (5) | |
| 2 | 4.48 | 14 | 8.96 | 100 80 (0) | | | 100 80 (0) | |
| 2 | 4.48 | 27 | 8.96 | 95 80 (0) | | | 100 80 (0) | |
| 2 | 4.48 | 4 | 8.96 | 70 80 (12) | | | 90 75 (0) | |
| 2 | 4.48 | 1 | 8.96 | 65 80 (18) | | | 95 75 (0) | |
| 2 | 4.48 | 22 | 8.96 | 70 70 (0) | | | 85 60 (0) | |
| 2 | 4.48 | 5 | 8.96 | 65 70 (7) | | | 70 60 (0) | |
| 2 | 4.48 | 18 | 8.96 | 55 85 (35) | | | 70 85 (17) | |
| 2 | 4.48 | 2 | 8.96 | 80 75 (0) | | | 95 75 (0) | |
| 2 | 4.48 | 16 | 8.96 | 80 80 | | | 55 75 | |

TABLE II-continued

| | | | | % PLANT INHIBITION AND % SAFENING EFFECT ( ) | | | | |
|---|---|---|---|---|---|---|---|---|
| | | | | | | GRAIN | | |
| HERBICIDE | | ANTIDOTE | | RICE | SORGHUM | WHEAT | SOYBEAN | CORN |
| NO. | RATE | NO. | RATE | W WO | W WO | W WO | W WO | W WO |
| 2 | 4.48 | 42 | 8.96 | 100 90 (0) | | | 100 90 (26) | |
| 2 | 4.48 | 21 | 8.96 | 95 90 (0) | | | 95 85 (0) | |
| 2 | 4.48 | 19 | 8.96 | 100 95 (0) | | | 90 90 (0) | |
| 2 | 4.48 | 13 | 8.96 | 100 85 (0) | | | 100 95 (0) | |
| 2 | 4.48 | 9 | 8.96 | 95 95 (0) | | | 100 90 (0) | |
| 2 | 4.48 | 30 | 8.96 | 90 95 (5) | | | 100 90 (0) | |
| 2 | 4.48 | 23 | 8.96 | 60 45 (0) | | | 95 80 (0) | |
| 2 | 4.48 | 10 | 8.96 | 95 95 (0) | | | 100 100 (0) | |
| 2 | 4.48 | 7 | 8.96 | 100 95 (0) | | | 100 95 (0) | |
| 2 | 4.48 | 11 | 8.96 | 100 95 (0) | | | 100 95 (0) | |
| 2 | 4.48 | 12 | 8.96 | 70 90 (22) | | | 100 95 (0) | |
| 2 | 4.48 | 26 | 8.96 | 95 90 (0) | | | 100 95 (0) | |
| 2 | 4.48 | 8 | 8.96 | | | | 100 80 (0) | |
| 2 | 4.48 | 37 | 8.96 | | | | 100 80 (0) | |
| 2 | 4.48 | 34 | 8.96 | 75 50 (0) | | | 85 90 (5) | |
| 2 | 4.48 | 38 | 8.96 | 100 75 (0) | | | 100 90 (0) | |
| 2 | 4.48 | 40 | 8.96 | 100 75 (0) | | | 100 90 (0) | |
| 2 | 4.48 | 36 | 8.96 | 20 75 (73) | | | 60 85 (29) | |
| 2 | 4.48 | 35 | 8.96 | 85 60 (0) | | | 100 70 (0) | |
| 2 | 4.48 | 32 | 8.96 | 85 60 (0) | | | 100 90 (0) | |
| 3 | 0.56 | 6 | 8.96 | 90 80 (0) | 80 80 (0) | 30 60 (50) | | |
| 3 | 1.12 | 6 | 8.96 | 100 85 (0) | 50 80 (37) | 35 75 (53) | | |
| 3 | 2.24 | 6 | 8.96 | 80 90 (11) | 45 75 (40) | 80 90 (11) | | |
| 3 | 2.24 | 6 | 8.96 | 100 99 (0) | 80 95 (15) | 80 90 (11) | | |
| 3 | 4.48 | 6 | 8.96 | 100 100 (0) | 85 98 (13) | 90 98 (8) | | |
| 3 | 2.24 | 33 | 8.96 | 80 90 (11) | 30 75 (60) | 100 90 (0) | | |
| 3 | 2.24 | 20 | 8.96 | | 80 95 (15) | 55 98 (43) | | |
| 3 | 2.24 | 24 | 8.96 | | 90 100 (10) | 60 85 (29) | | |
| 3 | 2.24 | 3 | 8.96 | | 80 90 (11) | 60 70 (14) | | |
| 3 | 2.24 | 39 | 8.96 | | 100 80 (0) | 95 80 (0) | | |
| 3 | 2.24 | 29 | 8.96 | | 60 90 (33) | 40 40 (0) | | |
| 3 | 2.24 | 25 | 8.96 | | 70 90 (22) | 80 95 (15) | | |
| 3 | 22.24 | 17 | 8.96 | | 95 100 (5) | 30 90 (66) | | |
| 3 | 2.24 | 15 | 8.96 | | 45 100 (55) | 80 90 (11) | | |
| 3 | 2.24 | 14 | 8.96 | | 85 100 (15) | 20 70 (71) | | |
| 3 | 2.24 | 27 | 8.96 | | 100 100 (0) | 75 70 (0) | | |
| 3 | 2.24 | 4 | 8.96 | | 80 95 (15) | 55 90 (38) | | |
| 3 | 2.24 | 1 | 8.96 | | 75 95 (21) | 80 90 (11) | | |

TABLE II-continued

% PLANT INHIBITION AND % SAFENING EFFECT ( )

| HERBICIDE | | ANTIDOTE | | RICE | GRAIN SORGHUM | WHEAT | SOYBEAN | CORN |
|---|---|---|---|---|---|---|---|---|
| NO. | RATE | NO. | RATE | W WO | W WO | W WO | W WO | W WO |
| 3 | 2.24 | 22 | 8.96 | | 85 95 (10) | 70 85 (17) | | |
| 3 | 2.24 | 5 | 8.96 | | 98 95 (0) | 75 85 (11) | | |
| 3 | 2.24 | 18 | 8.96 | | 100 75 (0) | 75 75 (0) | | |
| 3 | 2.24 | 2 | 8.96 | | 100 90 (0) | 90 90 (0) | | |
| 3 | 2.24 | 16 | 8.96 | | 100 70 (0) | 90 90 (0) | | |
| 3 | 2.24 | 42 | 8.96 | | 95 85 (0) | 90 100 (10) | | |
| 3 | 2.24 | 21 | 8.96 | | 90 85 (0) | 75 90 (16) | | |
| 3 | 2.24 | 19 | 8.96 | | 75 90 (16) | 90 95 (5) | | |
| 3 | 2.24 | 13 | 8.96 | | 95 95 (0) | 75 85 (11) | | |
| 3 | 2.24 | 9 | 8.96 | | 90 100 (10) | 100 95 (0) | | |
| 3 | 2.24 | 30 | 8.96 | | 100 100 (0) | 100 95 (0) | | |
| 3 | 2.24 | 23 | 8.96 | | 60 85 (29) | 70 55 (0) | | |
| 3 | 2.24 | 10 | 8.96 | | 90 90 (0) | 50 95 (47) | | |
| 3 | 2.24 | 7 | 8.96 | | 90 95 (5) | 80 95 (15) | | |
| 3 | 2.24 | 11 | 8.96 | | 100 95 (0) | 90 95 (5) | | |
| 3 | 2.24 | 12 | 8.96 | | 70 90 (22) | 100 85 (0) | | |
| 3 | 2.24 | 26 | 8.96 | | 90 90 (0) | 65 85 (23) | | |
| 3 | 2.24 | 8 | 8.96 | | 100 100 (0) | 20 90 (77) | | |
| 3 | 2.24 | 37 | 8.96 | | 95 100 (5) | 90 90 (0) | | |
| 3 | 2.24 | 34 | 8.96 | | 80 95 (15) | 90 85 (0) | | |
| 3 | 2.24 | 38 | 8.96 | | 65 95 (31) | 40 85 (52) | | |
| 3 | 2.24 | 40 | 8.96 | | 65 95 (31) | 90 85 (0) | | |
| 3 | 2.24 | 36 | 8.96 | | 55 90 (38) | 45 55 (18) | | |
| 3 | 2.24 | 35 | 8.96 | | 85 95 (10) | 80 60 (0) | | |
| 3 | 2.24 | 32 | 8.96 | | 90 75 (0) | 60 75 (20) | | |
| 4 | 4.48 | 6 | 8.96 | 70 50 (0) | 45 60 (25) | 25 70 (64) | | |
| 4 | 4.48 | 33 | 8.96 | 15 50 (70) | 60 60 (0) | 85 70 (0) | | |
| 4 | 6.72 | 20 | 8.96 | 95 90 (0) | | | | |
| 4 | 6.72 | 24 | 8.96 | 97 80 (0) | | | | |
| 4 | 6.72 | 3 | 8.96 | 95 85 (0) | | | | |
| 4 | 6.72 | 39 | 8.96 | 90 80 (0) | | | | |
| 4 | 6.72 | 29 | 8.96 | 75 75 (0) | | | | |
| 4 | 6.72 | 25 | 8.96 | 100 98 (0) | | | | |
| 4 | 4.48 | 17 | 8.96 | 95 90 (0) | | | | |
| 4 | 4.48 | 15 | 8.96 | 95 90 (0) | | | | |
| 4 | 4.48 | 14 | 8.96 | 95 90 (0) | | | | |
| 4 | 4.48 | 27 | 8.96 | 95 90 (0) | | | | |
| 4 | 4.48 | 4 | 8.96 | 100 85 (0) | | | | |
| 4 | 4.48 | 1 | 8.96 | 100 85 | | | | |

TABLE II-continued

% PLANT INHIBITION AND % SAFENING EFFECT ( )

| HERBICIDE | | ANTIDOTE | | RICE | SORGHUM | GRAIN WHEAT | SOYBEAN | CORN |
|---|---|---|---|---|---|---|---|---|
| NO. | RATE | NO. | RATE | W WO | W WO | W WO | W WO | W WO |
| 4 | 4.48 | 22 | 8.96 | 60 80 (25) | | | | |
| 4 | 4.48 | 5 | 8.96 | 98 80 (0) | | | | |
| 4 | 4.48 | 18 | 8.96 | 95 90 (0) | | | | |
| 4 | 4.48 | 2 | 8.96 | 95 90 (0) | | | | |
| 4 | 4.48 | 16 | 8.96 | 95 95 (0) | | | | |
| 4 | 4.48 | 42 | 8.96 | 65 90 (27) | | | | |
| 4 | 4.48 | 21 | 8.96 | 95 85 (0) | | | | |
| 4 | 4.48 | 19 | 8.96 | 100 90 (0) | | | | |
| 4 | 4.48 | 13 | 8.96 | 95 90 (0) | | | | |
| 4 | 4.48 | 9 | 8.96 | 80 95 (15) | | | | |
| 4 | 4.48 | 30 | 8.96 | 95 95 (0) | | | | |
| 4 | 4.48 | 23 | 8.96 | 85 90 (5) | | | | |
| 4 | 4.48 | 10 | 8.96 | 100 90 (0) | | | | |
| 4 | 4.48 | 7 | 8.96 | 100 95 (0) | | | | |
| 4 | 4.48 | 11 | 8.96 | 95 95 (0) | | | | |
| 4 | 4.48 | 12 | 8.96 | 90 95 (5) | | | | |
| 4 | 4.48 | 26 | 8.96 | 100 95 (0) | | | | |
| 4 | 4.48 | 8 | 8.96 | 70 80 (2) | | | | |
| 4 | 4.48 | 37 | 8.96 | 75 80 (6) | | | | |
| 4 | 4.48 | 34 | 8.96 | 75 85 (11) | | | | |
| 4 | 4.48 | 38 | 8.96 | 85 70 (0) | | | | |
| 4 | 4.48 | 40 | 8.96 | 75 70 (0) | | | | |
| 4 | 4.48 | 36 | 8.96 | 50 85 (41) | | | | |
| 4 | 4.48 | 35 | 8.96 | 95 75 (0) | | | | |
| 4 | 4.48 | 32 | 8.96 | 90 80 (0) | | | | |
| 5 | 1.12 | 20 | 8.96 | | | | | 90 90 (0) |
| 5 | 1.12 | 24 | 8.96 | | | | | 50 80 (37) |
| 5 | 1.12 | 3 | 8.96 | | | | | 95 95 (0) |
| 5 | 1.12 | 39 | 8.96 | | | | | 65 85 (23) |
| 5 | 1.12 | 29 | 8.96 | | | | | 50 70 (28) |
| 5 | 1.12 | 25 | 8.96 | | | | | 60 90 (33) |
| 5 | 2.24 | 17 | 8.96 | | | | | 80 90 (11) |
| 5 | 2.24 | 15 | 8.96 | | | | | 80 90 (11) |
| 5 | 2.24 | 14 | 8.96 | | | | | 80 85 (5) |
| 5 | 2.24 | 27 | 8.96 | | | | | 90 85 (0) |
| 5 | 2.24 | 4 | 8.96 | | | | | 75 95 (21) |
| 5 | 2.24 | 1 | 8.96 | | | | | 95 95 (0) |
| 5 | 2.24 | 22 | 8.96 | | | | | 95 80 (0) |

TABLE II-continued

% PLANT INHIBITION AND % SAFENING EFFECT ( )

| HERBICIDE NO. | RATE | ANTIDOTE NO. | RATE | RICE W WO | SORGHUM W WO | GRAIN WHEAT W WO | SOYBEAN W WO | CORN W WO |
|---|---|---|---|---|---|---|---|---|
| 5 | 8.96 | 5 | 8.96 | | | | | 95 |
| 5 | 2.24 | 18 | 8.96 | | | | | 90 90 (0) |
| 5 | 2.24 | 2 | 8.96 | | | | | 90 90 (0) |
| 5 | 2.24 | 16 | 8.96 | | | | | 80 75 (0) |
| 5 | 2.24 | 42 | 8.96 | | | | | 95 90 (0) |
| 5 | 2.24 | 21 | 8.96 | | | | | 95 90 (0) |
| 5 | 2.24 | 19 | 8.96 | | | | | 90 90 (0) |
| 5 | 2.24 | 13 | 8.96 | | | | | 85 90 (5) |
| 5 | 2.24 | 9 | 8.96 | | | | | 85 95 (10) |
| 5 | 2.24 | 30 | 8.96 | | | | | 100 95 (0) |
| 5 | 2.24 | 23 | 8.96 | | | | | 80 95 (15) |
| 5 | 2.24 | 10 | 8.96 | | | | | 45 95 (52) |
| 5 | 2.24 | 7 | 8.96 | | | | | 75 100 (25) |
| 5 | 2.24 | 11 | 8.96 | | | | | 100 100 (0) |
| 5 | 2.24 | 12 | 8.96 | | | | | 80 100 (20) |
| 5 | 2.24 | 26 | 8.96 | | | | | 95 100 (5) |
| 5 | 2.24 | 8 | 8.96 | | | | | 95 95 (0) |
| 5 | 2.24 | 37 | 8.96 | | | | | 90 95 (5) |
| 5 | 2.24 | 34 | 8.96 | | | | | 85 90 (5) |
| 5 | 2.24 | 38 | 8.96 | | | | | 90 90 (0) |
| 5 | 2.24 | 40 | 8.96 | | | | | 95 90 (0) |
| 5 | 2.24 | 36 | 8.96 | | | | | 100 85 (0) |
| 5 | 2.24 | 35 | 8.96 | | | | | 95 100 (5) |
| 5 | 2.24 | 32 | 8.96 | | | | | 100 95 (0) |

EXAMPLE VI

The following procedure shows interaction between a herbicide and antidote when the antidote is applied in a soil furrow containing crop seed and the herbicide is incorporated in a soil cover layer. Containers were filled and compacted with fumigated silt loam soil to a depth of about 1.3 cm from the top of the container. A first container was designated as an untreated control, a second container was designated as a herbicide control, and a third container was designated as a herbicide+antidote test container. Each container was seeded with crop seed in marked furrows. Antidote compound, dissolved in acetone, was applied directly to the seeded furrows of the third container. Antidote application rate was 0.55 mg active compound per inch of furrow. This rate was comparable to a plot application rate of 0.28 kilogram per hectare (Kg/ha) based on 76 cm (30") spaced-apart furrows. Then, each of the second and third containers was filled and leveled with a cover layer of soil having incorporated therein the selected herbicide at a pre-determined concentration. The first container was filled and leveled with soil containing no herbicide. The containers were then placed on a greenhouse bench and sub-irrigated as required for the duration of the test. Plant response was observed about three weeks after initial treatment. Results are reported in Table III.

TABLE III

% PLANT INHIBITION AND SAFENING EFFECT ( )

| HERBICIDE NO. | RATE | ANTIDOTE NO. | RATE | SORGHUM W WO | GRAIN WHEAT W WO | RICE W WO | SOYBEAN W WO | CORN W WO |
|---|---|---|---|---|---|---|---|---|
| 1 | 0.56 | 27 | 0.28 | | 90 95 (5) | | | |
| 1 | 0.56 | 5 | 0.28 | | 65 95 | | | |

TABLE III-continued

| | | | | % PLANT INHIBITION AND SAFENING EFFECT ( ) | | | | |
|---|---|---|---|---|---|---|---|---|
| | | | | | GRAIN | | | |
| HERBICIDE NO. | RATE | ANTIDOTE NO. | RATE | SORGHUM W WO | WHEAT W WO | RICE W WO | SOYBEAN W WO | CORN W WO |
| 1 | 0.56 | 30 | 0.28 | | 95 95 (31) (0) | | | |
| 1 | 0.56 | 26 | 0.28 | | 95 95 (0) | | | |
| 1 | 0.56 | 32 | 0.28 | | 85 95 (10) | | | |
| 1 | 0.56 | 31 | 0.28 | | 85 100 (15) | | | |
| 1 | 0.56 | 28 | 0.28 | | 70 95 (26) | | | |
| 1 | 0.56 | 41 | 0.28 | | 95 100 (5) | | | |
| 1 | 0.56 | 43 | 0.28 | | 40 100 (60) | | | |
| 2 | 4.48 | 27 | 0.28 | | | 100 95 (0) | 100 90 (0) | |
| 2 | 4.48 | 5 | 0.28 | | | 90 95 (5) | 100 90 (0) | |
| 2 | 4.48 | 30 | 0.28 | | | 95 95 (0) | 100 90 (0) | |
| 2 | 4.48 | 26 | 0.28 | | | 70 95 (26) | 90 90 (0) | |
| 2 | 4.48 | 32 | 0.28 | | | 85 95 (10) | 95 90 (0) | |
| 2 | 4.48 | 31 | 0.28 | | | 100 100 (0) | 95 95 (0) | |
| 2 | 4.48 | 28 | 0.28 | | | 60 75 (20) | 100 85 (0) | |
| 2 | 6.72 | 41 | 0.28 | | | 95 95 (0) | 100 100 (0) | |
| 2 | 6.72 | 43 | 0.28 | | | 95 95 (0) | 100 100 (0) | |
| 3 | 2.24 | 27 | 0.28 | 95 100 (5) | 80 80 (0) | | | |
| 3 | 2.24 | 5 | 0.28 | 75 100 (25) | 60 80 (25) | | | |
| 3 | 2.24 | 30 | 0.28 | 100 100 (0) | 80 80 (0) | | | |
| 3 | 2.24 | 26 | 0.28 | 100 100 (0) | 75 80 (6) | | | |
| 3 | 2.24 | 32 | 0.28 | 95 100 (5) | 70 80 (12) | | | |
| 3 | 2.24 | 31 | 0.28 | 95 100 (5) | 25 65 (61) | | | |
| 3 | 2.24 | 28 | 0.28 | 90 100 (10) | 95 95 (0) | | | |
| 3 | 2.24 | 41 | 0.28 | 95 100 (5) | 95 90 (0) | | | |
| 3 | 2.24 | 43 | 0.28 | 90 100 (10) | 45 85 (47) | | | |
| 4 | 4.48 | 27 | 0.28 | | | 95 85 (0) | | |
| 4 | 4.48 | 5 | 0.28 | | | 95 85 (0) | | |
| 4 | 4.48 | 30 | 0.28 | | | 95 85 (0) | | |
| 4 | 4.48 | 26 | 0.28 | | | 95 85 (0) | | |
| 4 | 4.48 | 32 | 0.28 | | | 95 85 (0) | | |
| 4 | 4.48 | 31 | 0.28 | | | 100 95 (0) | | |
| 4 | 4.48 | 28 | 0.28 | | | 90 95 (5) | | |
| 4 | 4.48 | 41 | 0.28 | | | 100 100 (0) | | |
| 4 | 4.48 | 43 | 0.28 | | | 80 95 (15) | | |
| 5 | 2.24 | 27 | 0.28 | | | | 65 50 (0) | 65 95 (31) |
| 5 | 2.24 | 5 | 0.28 | | | | 60 50 (0) | 50 95 (47) |
| 5 | 2.24 | 30 | 0.28 | | | | 65 50 (0) | 75 95 (21) |
| 5 | 2.24 | 26 | 0.28 | | | | 65 50 (0) | 95 95 (0) |

TABLE III-continued

| | | | | % PLANT INHIBITION AND SAFENING EFFECT ( ) | | | | |
|---|---|---|---|---|---|---|---|---|
| | | | | | | GRAIN | | |
| HERBICIDE NO. | RATE | ANTIDOTE NO. | RATE | SORGHUM W WO | WHEAT W WO | RICE W WO | SOYBEAN W WO | CORN W WO |
| 5 | 2.24 | 32 | 0.28 | | | | 95 50 (0) | 95 95 (0) |
| 5 | 2.24 | 31 | 0.28 | | | | 25 40 (37) | 75 100 (25) |
| 5 | 2.24 | 28 | 0.28 | | | | 50 40 (0) | 90 95 (5) |
| 5 | 2.24 | 41 | 0.28 | | | | 95 60 (0) | 20 95 (78) |
| 5 | 2.24 | 43 | 0.28 | | | | 95 60 (0) | 95 100 (5) |

EXAMPLE VII

The procedure of Example V was followed to determine the interaction between herbicide and antidote when both are incorporated in a soil cover layer before emergence of the crop species. In this series of tests, however, all containers were seeded with at least one weed species in addition to crop seed. Results are reported in Table IV.

TABLE IV

| | | | | % PLANT INHIBITION AND % SAFENING EFFECT ( ) | | | | | | | |
|---|---|---|---|---|---|---|---|---|---|---|---|
| HERBICIDE NO. | RATE | ANTIDOTE NO. | RATE | SOYBEAN W WO | BARN-YARD GRASS W WO | WILD OATS W WO | WHEAT W WO | GRAIN SORGHUM W WO | GREEN FOXTAIL W WO | RICE W WO | HEMP SESBANIA W WO | VEL-VET LEAF W WO |
| 1 | 0.28 | 20 | 8.96 | | | 100 100 (0) | 35 95 (63) | | | | | |
| 1 | 0.56 | 20 | 8.96 | | | 100 100 (0) | 80 90 (19) | | | | | |
| 1 | 1.12 | 20 | 8.96 | | | 100 100 (0) | 100 99 (0) | | | | | |
| 1 | 2.24 | 20 | 8.96 | | | 100 100 (0) | 100 100 (0) | | | | | |
| 1 | 0.28 | 17 | 8.96 | | | 99 100 (1) | 0 98 (100) | | | | | |
| 1 | 0.56 | 17 | 8.96 | | | 99 100 (1) | 50 99 (49) | | | | | |
| 1 | 1.12 | 17 | 8.96 | | | 100 100 (0) | 75 100 (25) | | | | | |
| 1 | 2.24 | 17 | 8.96 | | | 100 100 (0) | 90 100 (10) | | | | | |
| 1 | 0.28 | 15 | 8.96 | | | 95 100 (5) | 50 98 (48) | | | | | |
| 1 | 0.56 | 15 | 8.96 | | | 100 100 (0) | 80 99 (19) | | | | | |
| 1 | 1.12 | 15 | 8.96 | | | 100 100 (0) | 97 100 (3) | | | | | |
| 1 | 2.24 | 15 | 8.96 | | | 100 100 (0) | 100 100 (0) | | | | | |
| 1 | 0.28 | 14 | 8.96 | | | 99 99 (0) | 0 80 (100) | | | | | |
| 1 | 0.56 | 14 | 8.96 | | | 99 99 (0) | 0 97 (100) | | | | | |
| 1 | 1.12 | 14 | 8.96 | | | 99 100 (1) | 30 100 (70) | | | | | |
| 1 | 2.24 | 14 | 8.96 | | | 100 100 (0) | 80 100 (20) | | | | | |
| 1 | 0.28 | 4 | 8.96 | | | 99 100 (1) | 40 80 (50) | | | | | |
| 1 | 0.56 | 4 | 8.96 | | | 100 100 (0) | 60 95 (36) | | | | | |
| 1 | 1.12 | 4 | 8.96 | | | 100 100 (0) | 80 99 (19) | | | | | |
| 1 | 2.24 | 4 | 8.96 | | | 100 100 (0) | 90 100 (10) | | | | | |
| 1 | 0.14 | 12 | 2.24 | | | 90 100 (10) | 15 30 (50) | | | | | |
| 1 | 0.14 | 12 | 8.96 | | | 85 100 (15) | 0 30 (100) | | | | | |
| 1 | 0.56 | 12 | 2.24 | | | 100 100 (0) | 90 100 (10) | | | | | |
| 1 | 0.56 | 12 | 8.96 | | | 95 100 (5) | 80 100 (20) | | | | | |
| 1 | 0.14 | 8 | 2.24 | | | 95 100 (5) | 20 30 (33) | | | | | |
| 1 | 0.14 | 8 | 8.96 | | | 95 100 | 25 30 | | | | | |

TABLE IV-continued

% PLANT INHIBITION AND % SAFENING EFFECT ( )

| | | | | | (5) | (16) | | | | |
|---|---|---|---|---|---|---|---|---|---|---|
| 1 | 0.56 | 8 | 2.24 | | 100 100 | 95 100 | | | | |
| | | | | | (0) | (5) | | | | |
| 1 | 0.56 | 8 | 8.96 | | 100 100 | 90 100 | | | | |
| | | | | | (0) | (10) | | | | |
| 1 | 0.14 | 43 | 2.24 | | 100 100 | 35 50 | | | | |
| | | | | | (0) | (30) | | | | |
| 1 | 0.14 | 43 | 8.96 | | 25 100 | 10 50 | | | | |
| | | | | | (75) | (80) | | | | |
| 1 | 0.56 | 43 | 2.24 | | 100 100 | 85 100 | | | | |
| | | | | | (0) | (15) | | | | |
| 1 | 0.56 | 43 | 8.96 | | 100 100 | 50 100 | | | | |
| | | | | | (0) | (50) | | | | |
| 2 | 2.24 | 36 | 2.24 | 85 60 | | | | 50 45 | 100 100 | 100 100 |
| | | | | (0) | | | | (0) | (0) | (0) |
| 2 | 2.24 | 36 | 8.96 | 95 60 | | | | 50 45 | 100 100 | 100 100 |
| | | | | (0) | | | | (0) | (0) | (0) |
| 2 | 6.72 | 36 | 2.24 | 90 100 | | | | 70 80 | 100 100 | 100 100 |
| | | | | (10) | | | | (12) | (0) | (0) |
| 2 | 6.72 | 36 | 8.96 | 100 100 | | | | 60 80 | 100 100 | 100 100 |
| | | | | (0) | | | | (25) | (0) | (0) |
| 3 | 0.56 | 20 | 8.96 | | 20 60 | 40 20 | 99 100 | | | |
| | | | | | (66) | (0) | (1) | | | |
| 3 | 1.12 | 20 | 8.96 | | 40 70 | 50 60 | 98 100 | | | |
| | | | | | (42) | (16) | (2) | | | |
| 3 | 2.24 | 20 | 8.96 | | 80 95 | 99 90 | 100 100 | | | |
| | | | | | (15) | (0) | (0) | | | |
| 3 | 4.48 | 20 | 8.96 | | 70 90 | 80 96 | 97 100 | | | |
| | | | | | (22) | (16) | (3) | | | |
| 3 | 0.56 | 17 | 8.96 | | 0 50 | 95 95 | 98 85 | | | |
| | | | | | (100) | (0) | (0) | | | |
| 3 | 1.12 | 17 | 8.96 | | 10 65 | 100 97 | 99 98 | | | |
| | | | | | (84) | (0) | (0) | | | |
| 3 | 2.24 | 17 | 8.96 | | 35 90 | 100 98 | 100 98 | | | |
| | | | | | (61) | (0) | (0) | | | |
| 3 | 4.48 | 17 | 8.96 | | 60 98 | 100 100 | 100 100 | | | |
| | | | | | (38) | (0) | (0) | | | |
| 3 | 0.56 | 15 | 8.96 | | 0 50 | 60 95 | 98 85 | | | |
| | | | | | (100) | (36) | (0) | | | |
| 3 | 1.12 | 15 | 8.96 | | 0 65 | 75 97 | 98 98 | | | |
| | | | | | (100) | (22) | (0) | | | |
| 3 | 2.24 | 15 | 8.96 | | 80 90 | 97 98 | 100 98 | | | |
| | | | | | (11) | (1) | (0) | | | |
| 3 | 4.48 | 15 | 8.96 | | 80 98 | 98 100 | 100 100 | | | |
| | | | | | (18) | (2) | (0) | | | |
| 3 | 0.56 | 14 | 8.96 | | 0 75 | 25 50 | 99 98 | | | |
| | | | | | (100) | (50) | (0) | | | |
| 3 | 1.12 | 14 | 8.96 | | 35 90 | 40 95 | 100 99 | | | |
| | | | | | (61) | (57) | (0) | | | |
| 3 | 2.24 | 14 | 8.96 | | 65 90 | 70 90 | 100 99 | | | |
| | | | | | (27) | (22) | (0) | | | |
| 3 | 4.48 | 14 | 8.96 | | 75 100 | 90 90 | 100 100 | | | |
| | | | | | (25) | (0) | (0) | | | |
| 3 | 0.56 | 10 | 8.96 | | 85 80 | 75 95 | 100 35 | | | |
| | | | | | (0) | (21) | (0) | | | |
| 3 | 1.12 | 10 | 8.96 | | 40 70 | 75 100 | 100 75 | | | |
| | | | | | (42) | (25) | (0) | | | |
| 3 | 2.24 | 10 | 8.96 | | 90 100 | 90 95 | 100 90 | | | |
| | | | | | (10) | (5) | (0) | | | |
| 3 | 4.48 | 10 | 8.96 | | 95 95 | 100 100 | 100 95 | | | |
| | | | | | (0) | (0) | (0) | | | |
| 3 | 0.56 | 8 | 2.24 | | 30 60 | 90 95 | 100 100 | | | |
| | | | | | (50) | (5) | (0) | | | |
| 3 | 0.56 | 8 | 8.96 | | 10 60 | 40 95 | 100 100 | | | |
| | | | | | (83) | (57) | (0) | | | |
| 3 | 2.24 | 8 | 2.24 | | 95 90 | 100 100 | 100 100 | | | |
| | | | | | (0) | (0) | (0) | | | |
| 3 | 2.24 | 8 | 8.96 | | 90 90 | 90 100 | 100 100 | | | |
| | | | | | (0) | (10) | (0) | | | |
| 3 | 0.56 | 38 | 8.96 | | 25 40 | 40 65 | | | | |
| | | | | | (37) | (38) | | | | |
| 3 | 1.12 | 38 | 8.96 | | 40 50 | 75 70 | | | | |
| | | | | | (20) | (0) | | | | |
| 3 | 2.24 | 38 | 8.96 | | 75 70 | 80 90 | | | | |
| | | | | | (0) | (11) | | | | |
| 3 | 4.48 | 38 | 8.96 | | 80 75 | 95 95 | | | | |
| | | | | | (0) | (0) | | | | |
| 3 | 0.56 | 31 | 2.24 | | 0 35 | 85 95 | 100 100 | | | |
| | | | | | (100) | (10) | (0) | | | |
| 3 | 0.56 | 31 | 8.96 | | 35 35 | 90 95 | 100 100 | | | |
| | | | | | (0) | (5) | (0) | | | |

TABLE IV-continued

% PLANT INHIBITION AND % SAFENING EFFECT ( )

| HERBICIDE NO. | RATE | ANTIDOTE NO. | RATE | | | | WHEAT W WO | | GRAIN SORGHUM W WO | GREEN FOXTAIL W WO | | |
|---|---|---|---|---|---|---|---|---|---|---|---|---|
| 3 | 2.24 | 31 | 2.24 | | | | 90 90 (0) | | 100 100 (0) | 100 100 (0) | | |
| 3 | 2.24 | 31 | 8.96 | | | | 55 90 (38) | | 95 100 (5) | 100 100 (0) | | |
| 3 | 0.56 | 43 | 2.24 | | | | 85 80 (0) | | | 100 100 (0) | | |

| HERBICIDE NO. | RATE | ANTIDOTE NO. | RATE | SOYBEAN W WO | BARN-YARD GRASS W WO | WILD OATS W WO | WHEAT W WO | GRAIN SORGHUM W WO | GREEN FOXTAIL W WO | RICE W WO | HEMP SESBANIA W WO | CORN W WO |
|---|---|---|---|---|---|---|---|---|---|---|---|---|
| 3 | 0.56 | 43 | 8.96 | | | | 35 80 (56) | | 100 100 (0) | | | |
| 3 | 2.24 | 43 | 2.24 | | | | 90 95 (5) | | 100 100 (0) | | | |
| 3 | 2.24 | 43 | 8.96 | | | | 90 95 (5) | | 100 100 (0) | | | |
| 5 | 0.56 | 5 | 2.24 | | 100 100 (0) | | | | 100 100 (0) | | | 80 60 (0) |
| 5 | 0.56 | 5 | 8.96 | | 100 100 (0) | | | | 100 100 (0) | | | 35 60 (41) |
| 5 | 1.12 | 5 | 2.24 | 80 60 (0) | 100 100 (0) | | | | | | | |
| 5 | 1.12 | 5 | 8.96 | 75 60 (0) | 100 100 (0) | | | | | | | |
| 5 | 2.24 | 5 | 2.24 | | 100 100 (0) | | | | 100 100 (0) | | | 75 90 (16) |
| 5 | 2.24 | 5 | 2.24 | 85 70 (0) | 100 100 (0) | | | | | | | |
| 5 | 2.24 | 5 | 8.96 | | 100 100 (0) | | | | 100 100 (0) | | | 50 90 (44) |
| 5 | 2.24 | 5 | 8.96 | 90 70 (0) | 100 100 (0) | | | | | | | |
| 5 | 0.28 | 10 | 8.96 | | 100 100 (0) | | | | 100 99 (0) | | | 15 50 (70) |
| 5 | 0.56 | 10 | 8.96 | | 100 100 (0) | | | | 100 99 (0) | | | 35 75 (53) |
| 5 | 1.12 | 10 | 8.96 | | 100 100 (0) | | | | 100 100 (0) | | | 50 80 (37) |
| 5 | 2.24 | 10 | 8.96 | | 100 100 (0) | | | | 100 100 (0) | | | 95 95 (0) |
| 5 | 0.56 | 41 | 2.24 | | 100 100 (0) | | | | 100 100 (0) | | | 60 70 (14) |
| 5 | 0.56 | 41 | 8.96 | | 100 100 (0) | | | | 100 100 (0) | | | 80 70 (0) |
| 5 | 2.24 | 41 | 2.24 | | 100 100 (0) | | | | 100 100 (0) | | | 90 85 (0) |
| 5 | 2.24 | 41 | 8.96 | | 100 100 (0) | | | | 100 100 (0) | | | 95 85 (0) |
| 3 | 2.24 | 3 | 2.24 | 60 62 (3) | | 95 100 (s) | | | | | | |

| HERBICIDE NO. | RATE | ANTIDOTE NO. | RATE | SOYBEAN W WO | BARN-YARD GRASS W WO | WILD OATS W WO | WHEAT W WO | GRAIN SORGHUM W WO | GREEN FOXTAIL W WO | RICE W WO | HEMP SESBANIA W WO | VEL-VET LEAF W WO |
|---|---|---|---|---|---|---|---|---|---|---|---|---|
| 3 | 2.24 | 3 | 4.48 | 55 62 (11) | | 100 100 (0) | | | | | | |
| 3 | 2.24 | 3 | 8.96 | 60 62 (3) | 100 100 (0) | | | | | | | |
| 3 | 4.48 | 3 | 2.24 | 35 55 (36) | | 90 100 (10) | | | | | | |
| 3 | 4.48 | 3 | 4.48 | 55 55 (0) | | 100 100 (0) | | | | | | |
| 3 | 4.48 | 3 | 8.96 | 40 55 (27) | | 100 100 (0) | | | | | | |
| 3 | 2.24 | 4 | 2.24 | 35 62 (43) | 95 100 (5) | | | | | | | |
| 3 | 2.24 | 4 | 4.48 | 60 62 (3) | 95 100 (5) | | | | | | | |
| 3 | 2.24 | 4 | 8.96 | 40 62 (35) | 90 100 (10) | | | | | | | |
| 3 | 4.48 | 4 | 2.24 | 35 55 (36) | 100 100 (0) | | | | | | | |
| 3 | 4.48 | 4 | 4.48 | 65 55 (0) | 100 100 (0) | | | | | | | |
| 3 | 4.48 | 4 | 8.96 | 15 55 (72) | 95 100 (5) | | | | | | | |
| 3 | 2.24 | 22 | 2.24 | 55 62 (11) | 90 100 (10) | | | | | | | |

TABLE IV-continued

% PLANT INHIBITION AND % SAFENING EFFECT ( )

| HERBICIDE NO. | RATE | ANTIDOTE NO. | RATE | WHEAT W WO | DOWNY BROME W WO | WILD OATS W WO | GREEN FOXTAIL W WO |
|---|---|---|---|---|---|---|---|
| 3 | 2.24 | 22 | 4.48 | 20 62 (67) | | 75 100 (25) | |
| 3 | 2.24 | 22 | 8.96 | 35 62 (43) | | 85 100 (15) | |
| 3 | 4.48 | 22 | 2.24 | | 50 55 (9) | | 100 100 (0) |
| 3 | 4.48 | 22 | 4.48 | | 50 55 (9) | | 100 100 (0) |
| 3 | 4.48 | 22 | 8.96 | | 20 55 (63) | | 100 100 (0) |
| 3 | 2.24 | 5 | 2.24 | | 40 62 (35) | | 100 100 (0) |
| 3 | 2.24 | 5 | 4.48 | | 50 62 (19) | | 95 100 (5) |
| 3 | 2.24 | 5 | 8.96 | | 30 62 (51) | | 100 100 (0) |
| 3 | 4.48 | 5 | 2.24 | | 40 55 (27) | | 100 100 (0) |
| 3 | 4.48 | 5 | 4.48 | | 30 55 (45) | | 100 100 (0) |
| 3 | 4.48 | 5 | 8.96 | | 25 55 (54) | | 90 100 (10) |

The foregoing examples illustrate that the combinations of herbicide and antidote of this invention are useful in controlling weeds while reducing herbicidal injury to crop plants under greenhouse test conditions.

In field applications, the herbicide, antidote, or a mixture thereof, may be applied to the plant locus without any adjuvants other than a solvent. Usually, the herbicide, antidote, or a mixture thereof, is applied in conjunction with one or more adjuvants in liquid or solid form. Compositions or formulations containing mixtures of an appropriate herbicide and antidote usually are prepared by admixing the herbicide and antidote with one or more adjuvants such as diluents, solvents, extenders, carriers, conditioning agents, water, wetting agents, dispersing agents, or emulsifying agents, or any suitable combination of these adjuvants. These mixtures may be in the form of particulate solids, granules, pellets, wettable powders, dusts, solutions, aqueous dispersions, or emulsions.

Examples of suitable adjuvants are finely-divided solid carriers and extenders including talcs, clays, pumice, silica, diatomaceous earth, quartz, Fuller's earth, sulfur, powdered cork, powdered wood, walnut flour, chalk, tobacco dust, charcoal, and the like. Typical liquid diluents include Stoddard's solvent, acetone, methylene chloride, alcohols, glycols, ethyl acetate, benzene, and the like. Liquids and wettable powders usually contain as a conditioning agent one or more surface-active agents in amounts sufficient to make a composition readily dispersible in water or in oil. The term "surface-active agent" includes wetting agents, dispersing agents, suspending agents, and emulsifying agents. Typical surface-active agents are mentioned in U.S. Pat. No. 2,547,724.

Compositions of this invention generally contain from about 5 to 95 parts herbicide-and-antidote, about 1 to 50 parts surface-active agent, and about 4 to 94 parts solvent, all parts being by weight based on the total weight of the composition.

Application of the herbicide, antidote, or mixture thereof, can be carried out by conventional techniques utilizing, for example, hand-carried or tractor-mounted spreaders, power dusters, boom and hand sprayers, spray dusters, and granular applicators. If desired, application of the compositions of the invention to plants can be accomplished by incorporating the compositions in the soil or other media.

The crop may be protected by treating the crop seed with an effective amount of antidote prior to planting. Generally, smaller amounts of antidote are required to treat such seeds. A weight ratio of as little as 0.6 parts of antidote per 1000 parts of seed may be effective. The amount of antidote utilized in treating the seed may be increased if desired. Generally, however, a weight ratio of antidote-to-seed weight may range from 0.1 to 10.0 parts of antidote per 1000 parts of seed. Since only a very small amount of active antidote is usually required for the seed treatment, the compound preferably is formulated as an organic solution, powder, emulsifiable concentrate, water solution, or flowable formulation, which can be diluted with water by the seed treater for use in seed treating apparatus. Under certain conditions, it may be desirable to dissolve the antidote in an organic solvent or carrier for use as a seed treatment or the pure compound alone may be used under properly controlled conditions.

For antidote seed-coating or for antidotes applied to soil in granular or liquid formulations, suitable carriers may be either solids, such as talc, sand, clay, diatomaceous earth, sawdust, calcium carbonate, and the like, or liquids, such as water, kerosene, acetone, benzene, toluene, xylene, and the like, in which the active antidote may be either dissolved or dispersed. Emulsifying agents are used to achieve a suitable emulsion if two immiscible liquids are used as a carrier. Wetting agents may also be used to aid in dispersing the active antidote in liquids used as a carrier in which the antidote is not completely soluble. Emulsifying agents and wetting agents are sold under numerous tradenames and trademarks and may be either pure compounds, mixtures of compounds of the same general groups, or they may be mixtures of compounds of different classes. Typical satisfactory surface active agents which may be used are alkali metal higher-alkylarylsulfonates such as sodium dodecylbenzenesulfonate and the sodium salts of alkylnaphthalenesulfonic acids, fatty alcohol sulfates such as the sodium salts of monoesters of sulfuric acid with n-aliphatic alcohols containing 8–18 carbon atoms, long-chain quaternary ammonium compounds, sodium salts of petroleum-derived alkylsulfonic acids, polyethylene sorbitan monooleate, alkylaryl polyether alcohols, water-soluble lignin sulfonate salts, alkali casein compositions, long-chain alcohols usually containing 10–18 carbon atoms, and condensation products of ethylene oxide with fatty acids, alkylphenols, and mercaptans.

Although this invention has been described with respect to specific embodiments, the details of these embodiments are not to be construed as limitations. Various equivalents, changes, and modifications may be made without departing from the spirit and scope of this invention, and it is understood that such equivalent embodiments are part of this invention.

What is claimed is:

1. A method for reducing herbicide injury to a crop plant due to application of a herbicidally-effective amount of a herbicide compound selected from thiocarbamates, triazines and acetamides which method comprises applying to the plant locus a safening-effective amount of at least one antidote compound of the structural formula

wherein A is selected from phenyl, naphthyl, and

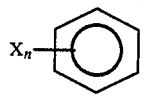

wherein each of $X_n$ is independently selected from halo, alkyl, haloalkyl, alkoxy, alkoxycarbonyl, carboxylic acid, nitro, cyano, cyanocycloalkyl, and phenoxy, with "n" being an integer from one through five; wherein R is selected from cyano, carboxylic acid, carboxamide, and N-hydroxycarboximidamide.

2. The method of claim 1 wherein said antidote compound is of the formula wherein A is selected from 2-naphthyl and

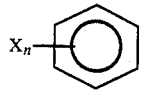

wherein each of $X_n$ is independently selected from halo, alkyl of one to five carbon atoms, perhaloalkyl of one to three carbon atoms, cyano and cyanocycloalkyl, with "n" being one or two; and wherein R is cyano.

3. The method of claim 2 wherein said antidote compound is of the formula wherein $X_n$ is one or more groups independently selected from halo and trifluoromethyl, with "n" being one or two.

4. The method of claim 1 wherein said herbicide compound is alachlor, said crop plant is wheat, and said antidote compound is selected from
1-(4-chlorophenyl)cyclopropanecarbonitrile,
1-(4-chlorophenyl)cyclopropanecarboxylic acid,
1-[3-(trifluoromethyl)phenyl]cyclopropanecarbonitrile,
1-(2,6-dichlorophenyl)cyclopropanecarbonitrile,
1-(2,4-dichlorophenyl)cyclopropanecarbonitrile,
1-(2-chloro-6-fluorophenyl)cyclopropanecarbonitrile,
1-(2-chlorophenyl)cyclopropanecarbonitrile,
1-(2-methylphenyl)cyclopropanecarbonitrile,
1-(3-chlorophenyl)cyclopropanecarbonitrile,
1-(2-iodophenyl)cyclopropanecarbonitrile,
1-(3-bromophenyl)cyclopropanecarbonitrile,
1-(4-iodophenyl)cyclopropanecarboxylic acid,
1-(3-phenoxyphenyl)cyclopropanecarbonitrile,
1-(2-bromophenyl)-N-hydroxycyclopropanecarboximidamide.

5. The method of claim 1 wherein said herbicide compound is triallate, said crop plant is wheat, and said antidote compound is selected from
1-[3-(trifluoromethyl)phenyl]cyclopropanecarbonitrile,
1-(2,6-dichlorophenyl)cyclopropanecarbonitrile,
1-(2,4-dichlorophenyl)cyclopropanecarbonitrile,
1-(2-chloro-6-fluorophenyl)cyclopropanecarbonitrile,
1-(2-chlorophenyl)cyclopropanecarbonitrile,
1-[4-(trifluoromethyl)phenyl]cyclopropanecarbonitrile,
1-(2-iodophenyl)cyclopropanecarbonitrile,
1-(4-iodophenyl)cyclopropanecarbonitrile,
1-(3-bromophenyl)cyclopropanecarbonitrile,
1-(2-bromophenyl)-N-hydroxycyclopropanecarboximidamide.

6. The method of claim 1 wherein said herbicide compound is alachlor, said crop plant is grain sorghum, and said antidote compound is selected from 1-(4-chlorophenyl)cyclopropanecarbonitrile, 1-(4-chlorophenyl)cyclopropanecarboxylic acid, 1-(2,4-dichlorophenyl)cyclopropanecarbonitrile.

7. The method of claim 1 wherein said herbicide compound is selected from acetochlor and 2-chloro-2'-methyl-6'-methoxy-N-(isopropoxymethyl)acetanilide, said crop plant is corn, and said antidote compound is selected from 1-(3-chlorophenyl)cyclopropanecarbonitrile and 1-(2-iodophenyl)cyclopropanecarbonitrile.

8. The method of claim 1 wherein said herbicide is butachlor, said crop plant is rice and said antidote compound is selected from 1-(4-chlorophenyl)cyclopropanecarbonitrile, 1-(4-chlorophenyl)cyclopropanecarboxylic acid and 1-(2-iodophenyl)cyclopropanecarboxylic acid.

9. The method of claim 1 wherein A is selected from 1-naphthyl and

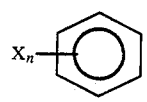

wherein each of $X_n$ is independently selected from fluoro, chloro, iodo and carboxylic acid, with "n" being one or two; and wherein R is selected from carboxylic acid, carboxamide and N-hydroxycarboximidamide.

10. The method of claim 9 wherein said antidote compound is 1-(4-iodophenyl)cyclopropanecarboxylic acid.

11. A combination of a herbicidally-effective amount of a herbicide compound selected from thiocarbamates, triazines and acetamides and a safening-effective amount of an antidote compound of the structural formula

wherein A is selected from phenyl, naphthyl, and

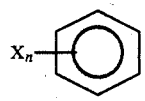

wherein each of $X_n$ is independently selected from halo, alkyl, haloalkyl, alkoxy, alkoxycarbonyl, carboxylic acid, nitro, cyano, cyanocycloalkyl, and phenoxy, with "n" being an integer from one through five; wherein R is selected from cyano, carboxylic acid, carboxamide, and N-hydroxycarboximidamide.

12. The combination of claim 11 wherein said antidote compound is of the formula wherein A is selected from 2-naphthyl and

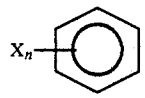

wherein each of $X_n$ is independently selected from halo, alkyl of one to five carbon toms, perhaloalkyl of one to three carbon atoms, cyano and cyanocycloalkyl, with "n" being one or two; and wherein R is cyano.

13. The combination of claim 12 wherein said antidote compound is of the formula where $X_n$ is one or more groups independently selected from halo and trifluoromethyl, with "n" being one or two.

14. The combination of claim 11 wherein said herbicide compound is alachlor and said antidote compound is selected from
1-(4-chlorophenyl)cyclopropanecarbonitrile,
1-(4-chlorophenyl)cyclopropanecarboxylic acid,
1-[3-(trifluoromethyl)phenyl]cyclopropanecarbonitrile,
1-(2,6-dichlorophenyl)cyclopropanecarbonitrile,
1-(2,4-dichlorophenyl)cyclopropanecarbonitrile,
1-(2-chloro-6-fluorophenyl)cyclopropanecarbonitrile,
1-(2-chlorophenyl)cyclopropanecarbonitrile,
1-(2-methylphenyl)cyclopropanecarbonitrile,
1-(3-chlorophenyl)cyclopropanecarbonitrile,
1-(2-iodophenyl)cyclopropanecarbonitrile,
1-(3-bromophenyl)cyclopropanecarbonitrile,
1-(4-iodophenyl)cyclopropanecarboxylic acid,
1-(3-phenoxyphenyl)cyclopropanecarbonitrile,
1-(2-bromophenyl)-N-hydroxycyclopropanecarboximidamide.

15. The combination of claim 11 wherein said herbicide compound is triallate and said antidote compound is selected from
1-[3-(trifluoromethyl)phenyl]cyclopropanecarbonitrile,
1-(2,6-dichlorophenyl)cyclopropanecarbonitrile,
1-(2,4-dichlorophenyl)cyclopropanecarbonitrile,
1-(2-chloro-6-fluorophenyl)cyclopropanecarbonitrile,
1-(2-chlorophenyl)cyclopropanecarbonitrile,
1-[4-(trifluoromethyl)phenyl]cyclopropanecarbonitrile,
1-(2-iodophenyl)cyclopropanecarbonitrile,
1-(4-iodophenyl)cyclopropanecarbonitrile,
1-(3-bromophenyl)cyclopropanecarbonitrile,
1-(2-bromophenyl)-N-hydroxycyclopropanecarboximidamide.

16. The combination of claim 11 wherein said herbicide compound is alachlor and said antidote compound is selected from
1-(4-chlorophenyl)cyclopropanecarbonitrile,
1-(4-chlorophenyl)cyclopropanecarboxylic acid,
1-(2,4-dichlorophenyl)cyclopropanecarbonitrile.

17. The combination of claim 11 wherein said herbicide compound is selected from acetochlor and 2-chloro-2'-methyl-6'-methoxy-N-(isopropoxymethyl)acetanilide and said antidote compound is selected from 1-(3-chlorophenyl)cyclopropanecarbonitrile and 1-(2-iodophenyl)cyclopropanecarbonitrile.

18. The combination of claim 11 wherein said herbicide is butachlor and said antidote compound is selected from 1-(4-chlorophenyl)cyclopropanecarbonitrile, 1-(4-chlorophenyl)cyclopropanecarboxylic acid and 1-(2-iodophenyl)cyclopropanecarboxylic acid.

19. The combination of claim 11 wherein A is selected from 1-naphthyl and

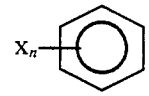

wherein each of $X_n$ is independently selected from fluoro, chloro, iodo and carboxylic acid, with "n" being one or two; and wherein R is selected from carboxylic acid, carboxamide and N-hydroxycarboximidamide.

20. The combination of claim 19 wherein said antidote compound is 1-(4-iodophenyl)cyclopropanecarboxylic acid.

21. A herbicide comprising triallate and an antiantidotally-effective amount of 1-[3-(trifluoromethyl)phenyl]cyclopropanecarbonitrile.

22. A herbicide comprising triallate and an antiantidotally-effective amount of 1-(2,6-dichlorophenyl)cyclopropanecarbonitrile.

23. A herbicide comprising triallate and an antiantidotally-effective amount of 1-(2-chloro-6-fluorophenyl)cyclopropanecarbonitrile.

24. A herbicide comprising triallate and an antiantidotally-effective amount of 1-(2-chlorophenyl)cyclopropanecarbonitrile.

25. A herbicide comprising triallate and an antiantidotally-effective amount of 1-[4-(trifluoromethyl)phenyl]cyclopropanecarbonitrile.

26. A herbicide comprising triallate and an antiantidotally-effective amount of 1-(4-iodophenyl)cyclopropanecarbonitrile.

27. A herbicide comprising triallate and an antiantidotally-effective amount of 1-(3-bromophenyl)cyclopropanecarbonitrile.

28. A herbicide comprising alachlor and an antiantidotally-effective amount of 1-[3-(trifluoromethyl)phenyl]cyclopropanecarbonitrile.

29. A herbicide comprising alachlor and an antiantidotally-effective amount of 1-(2,6-dichlorophenyl)cyclopropanecarbonitrile.

30. A herbicide comprising alachlor and an antiantidotally-effective amount of 1-(2-chloro-6-fluorophenyl)cyclopropanecarbonitrile.

31. A herbicide comprising alachlor and an antiantidotally-effective amount of 1-(3-bromophenyl)cyclopropanecarbonitrile.

* * * * *